US011961590B2

(12) United States Patent
Jang

(10) Patent No.: US 11,961,590 B2
(45) Date of Patent: Apr. 16, 2024

(54) METHODS FOR PREPARING OPTIMAL COMBINATION OF OLIGONUCLEOTIDES

(71) Applicant: SEEGENE, INC., Seoul (KR)

(72) Inventor: Mi Hyun Jang, Seoul (KR)

(73) Assignee: SEEGENE, INC., Seoul (KR)

( * ) Notice: Subject to any disclaimer, the term of this patent is extended or adjusted under 35 U.S.C. 154(b) by 1215 days.

(21) Appl. No.: 16/605,298

(22) PCT Filed: Apr. 17, 2018

(86) PCT No.: PCT/KR2018/004434
§ 371 (c)(1),
(2) Date: Oct. 15, 2019

(87) PCT Pub. No.: WO2018/194342
PCT Pub. Date: Oct. 25, 2018

(65) Prior Publication Data

US 2020/0058370 A1 Feb. 20, 2020

(30) Foreign Application Priority Data

Apr. 17, 2017 (KR) ........................ 10-2017-0049350

(51) Int. Cl.
*G01N 33/48* (2006.01)
*C12N 15/10* (2006.01)
(Continued)

(52) U.S. Cl.
CPC ......... *G16B 25/20* (2019.02); *C12N 15/1089* (2013.01); *G06F 17/12* (2013.01); *G16B 30/00* (2019.02)

(58) Field of Classification Search
CPC .... G16B 25/20; G16B 30/00; C12N 15/1089; G06F 17/12
See application file for complete search history.

(56) References Cited

U.S. PATENT DOCUMENTS 6,506,735 B1 1/2003 MacLeod
8,318,423 B2 11/2012 Lee et al.
(Continued)

FOREIGN PATENT DOCUMENTS

CA 2146160 A1 5/1994

OTHER PUBLICATIONS

Craig et al. Ordering of cosmid clones covering the Herpes simplex virus (HSV-I) genome: a test case for fingerprinting by hybridisation. Nucleic Acids Research, vol. 18, pp. 2653-2660. (Year: 1990).*
(Continued)

*Primary Examiner* — Russell S Negin
(74) *Attorney, Agent, or Firm* — Harness, Dickey & Pierce, P.L.C.

(57) ABSTRACT

The present invention relates to optimization logic for preparing an optimal combination of oligonucleotides hybridized with a plurality of target nucleic acid sequences, in a completely different approach from conventional methods, i.e., empirical and manual methods. In addition, the optimization logic of the present invention may be used to (i) preparing an oligonucleotide combination used to detect a plurality of target nucleic acid sequences with a target coverage of interest, (ii) selecting target nucleic acid sequences to be detected by a multiplex target detection with a highest target coverage by using a limited number of oligonucleotides, and (iii) determining a conserved region in a plurality of target nucleic acid sequences.

11 Claims, 4 Drawing Sheets

Specification includes a Sequence Listing.

(51) Int. Cl.
*G01N 33/50* (2006.01)
*G06F 17/12* (2006.01)
*G16B 25/20* (2019.01)
*G16B 30/00* (2019.01)

(56) References Cited

U.S. PATENT DOCUMENTS

| | | | |
|---|---|---|---|
| 8,685,649 | B2 | 4/2014 | Dauner et al. |
| 8,735,063 | B2 | 5/2014 | Beld et al. |
| 2005/0089889 | A1 | 4/2005 | Ramsing et al. |
| 2006/0008810 | A1 | 1/2006 | Lee et al. |
| 2010/0196876 | A1 | 8/2010 | Hnatyszyn et al. |
| 2011/0306036 | A1 | 12/2011 | Dauner et al. |
| 2016/0306915 | A1 | 10/2016 | Kim et al. |

OTHER PUBLICATIONS

D. Lipson et al: "Optimization of probe covereage for high-resolution oligonucleotide aCGH", Bioinformatics vol. 23, No. 2. Jan. 15, 2007.

Alexander Loy et al: "probeCheck—a central resource for evaluating oligonucleotide probe coverage and specificity: probeCheck—an online probe match tool". Jul. 21, 2008.

Hajiaghayi M T et al: "Minimum Multicolored Subgraph Problem in Multiplex PCR Primer Set Selection and Population Haplotyping" May 28, 2006.

Supplementary European Search Report from European Patent Application No. EP18788341.

Feng, Shengzhong et al: "A fast and flexible approach to oligonucleotide probe design for genomes and gene families", Bioinformatics vol. 23, No. 10. Mar. 28, 2007.

Won-Hyung Chung et al: "Design of long oligonucleotide probes for functional gene detection in a microbial community" Bioinformatics vol. 21, No. 22. Sep. 13, 2005.

Office Action from Korean Patent Application No. KR10-2019-7032056 filed Oct. 29, 2021.

International Search Report from corresponding PCT Application No. PCT/KR2018/004434, dated Mar. 4, 2019.

Li, X., et al.; "Selection of optimal oligonucleotide probes for microarrays using multiple criteria, global alignment and parameter estimation", Nucleic Acids Research, 2005, vol. 33, No. 19, pp. 6114-6123.

Bastien, N., et al.; "Genetic Variability of the G Glycoprotein Gene of Human Metapneumovirus", Journal of Clinical Microbiology, Aug. 2004, pp. 3532-3537.

Peret, T. C. T., et al.; "Characterization of Human Metapneumoviruses Isolated from Patients in North America", The Journal of Infectious Diseases, 2002, 185, pp. 1660-1663.

Ebihara, T., et al.; "Human Metapneumovirus Infection in Japanese Children", Journal of Clinical Microbiology, vol. 42, No. 1, Jan. 2004, pp. 126-132.

Jenny-Avital, E. R., et al.; "Erroneously Low or Undetectable Plasma Human Immunodeficiency Virus Type 1 (HIV-1) Ribonucleic Acid Load, Determined by Polymerase Chain Reaction, in West African and American Patients with Non-B Subtype HIV-1 Infection", Clinical Infectious Diseases, 2001, 32, pp. 1227-1230.

Duffy, S., et al.; "Rates of evolutionary change in viruses: patterns and determinants", Nature Reviews—Genetics, vol. 9, Apr. 2008, pp. 267-276.

Tong, Y. G., et al.; "Genetic diversity and evolutionary dynamics of Ebola virus in Sierra Leone", Nature, 2015, pp. 1-11.

Tong, Y. G., et al.; "Erratum: Genetic diversity and evolutionary dynamics of Ebola virus in Sierra Leone", Nature 524, 93-96 (2015).

* cited by examiner

Fig. 2

| | Probe1 | Probe2 | Probe3 | Probe4 | Probe5 | Probe6 | Probe7 | Probe8 | Probe9 | Probe10 |
|---|---|---|---|---|---|---|---|---|---|---|
| Seq1 | 0 | 0 | 0 | 0 | 0 | 0 | 0 | 0 | 0 | 0 |
| Seq2 | 0 | 0 | 0 | 0 | 0 | 0 | 0 | 0 | 0 | 0 |
| Seq3 | 0 | 0 | 0 | 0 | 0 | 0 | 0 | 0 | 0 | 0 |
| Seq4 | 0 | 0 | 0 | 0 | 0 | 0 | 0 | 0 | 0 | 0 |
| Seq5 | 0 | 0 | 0 | 0 | 0 | 0 | 0 | 0 | 0 | 0 |
| Seq6 | 0 | 0 | 0 | 0 | 0 | 0 | 0 | 0 | 0 | 0 |
| Seq7 | 0 | 0 | 0 | 0 | 0 | 0 | 0 | 0 | 0 | 0 |
| Seq8 | 0 | 0 | 0 | 0 | 0 | 0 | 0 | 0 | 0 | 0 |
| Seq9 | 0 | 0 | 0 | 0 | 0 | 0 | 0 | 0 | 0 | 0 |
| Seq10 | 0 | 0 | 0 | 0 | 0 | 0 | 0 | 0 | 0 | 0 |
| Seq11 | 1 | 1 | 1 | 1 | 0 | 1 | 1 | 0 | 0 | 1 |
| Seq12 | 1 | 1 | 1 | 1 | 0 | 1 | 1 | 0 | 0 | 1 |
| Seq13 | 1 | 1 | 1 | 1 | 0 | 1 | 1 | 0 | 0 | 1 |
| Seq14 | 1 | 1 | 1 | 1 | 0 | 1 | 1 | 0 | 0 | 1 |
| Seq15 | 0 | 0 | 0 | 0 | 0 | 0 | 0 | 0 | 0 | 0 |

Fig. 3

| | | | | | | | | | | |
|---|---|---|---|---|---|---|---|---|---|---|
| Seq1 | | | | | | Probe6 | Probe7 | | Probe9 | |
| Seq2 | | | | Probe4 | | | | | | |
| Seq3 | | | | | | Probe6 | | Probe8 | | |
| Seq4 | | | | | | | | Probe8 | | Probe10 |
| Seq5 | | Probe2 | | | | | | | | |
| Seq6 | | | | | | | Probe7 | | | |
| Seq7 | Probe1 | Probe2 | Probe3 | Probe4 | Probe5 | Probe6 | | Probe8 | Probe9 | Probe10 |
| Seq8 | | Probe2 | Probe3 | | | | Probe7 | | | |
| Seq9 | Probe1 | Probe2 | | | Probe5 | Probe6 | | | | |
| Seq10 | | Probe2 | | | | | Probe7 | | | |

| | Probe1 | Probe2 | Probe3 | Probe4 | Probe5 | Probe6 | Probe7 | Probe8 | Probe9 | Probe10 |
|---|---|---|---|---|---|---|---|---|---|---|
| Seq1 | 0 | 0 | 0 | 0 | 0 | 1 | 1 | 0 | 1 | 0 |
| Seq2 | 0 | 0 | 0 | 1 | 0 | 0 | 0 | 0 | 0 | 0 |
| Seq3 | 0 | 0 | 0 | 0 | 0 | 1 | 0 | 1 | 0 | 0 |
| Seq4 | 0 | 0 | 0 | 0 | 0 | 0 | 0 | 1 | 0 | 1 |
| Seq5 | 0 | 1 | 0 | 0 | 0 | 0 | 0 | 0 | 0 | 0 |
| Seq6 | 0 | 0 | 0 | 0 | 0 | 0 | 1 | 0 | 0 | 0 |
| Seq7 | 1 | 1 | 1 | 1 | 1 | 1 | 0 | 1 | 1 | 1 |
| Seq8 | 0 | 1 | 1 | 0 | 0 | 0 | 1 | 0 | 0 | 0 |
| Seq9 | 1 | 1 | 0 | 0 | 1 | 1 | 0 | 0 | 0 | 0 |
| Seq10 | 0 | 1 | 0 | 0 | 0 | 0 | 1 | 0 | 0 | 0 |

METHODS FOR PREPARING OPTIMAL COMBINATION OF OLIGONUCLEOTIDES

CROSS-REFERENCE TO RELATED APPLICATIONS

This application is a national phase application of PCT Application No. PCT/KR2018/004434 filed on Apr. 17, 2018, which claims priority to Korean Patent Application No. 10-2017-0049350 filed on Apr. 17, 2017. The entire disclosures of the applications identified in this paragraph are incorporated herein by reference.

BACKGROUND OF THE INVENTION

Field of the Invention

The present invention relates to technology for preparing an optimal combination of oligonucleotides for detecting a plurality of target nucleic acid sequences.

Description of the Related Art

A variety of techniques have been developed to detect target nucleic acid molecules of pathogens and identify these target nucleic acid molecules, and these are collectively referred to as molecular diagnostics. Most of the molecular diagnostic techniques use oligonucleotides such as primers and probes hybridizable with target nucleic acid molecules.

To date, molecular diagnostic technologies have made many advances. However, there are still technical challenges to be solved in the diagnosis of pathogens having genomes that exhibit genetic diversity or genetic variability.

Genetic diversity or genetic variability has been reported in various genomes. In particular, genetic diversity is most frequently found and occurs in viral genomes (Bastien N. et al., Journal of Clinical Microbiology, 42:3532 (2004); Peret T C. et al., Journal of Infectious Diseases, 185:1660 (2002); Ebihara T. et al., Journal of Clinical Microbiology, 42:126 (2004); Jenny-Avital E R. et al. Clinical Infectious Diseases, 32:1227 (2001); Duffy S. et. al., Nat. Rev. Genet. 9(4):267-76(2008); Tong Y G et. al., Nature. 22:526 (2015)).

In detecting a pathogen with genetic diversity, designing oligonucleotides with taking into account a certain sequence of a target nucleic acid molecule of this pathogen is very likely to lead to false negative results. Thus, in order to determine whether a certain pathogen is present in an unknown sample, probes or primers should be designed in consideration of all nucleic acid sequences or as many nucleic acid sequences as possible of known genetic diversity for one target nucleic acid molecule of this certain pathogen. In order to detect a target nucleic acid molecule exhibiting such genetic diversity, two approaches have been largely developed.

The first method detects a target nucleic acid molecule using a plurality of oligonucleotides that are hybridized with a plurality of nucleic acid sequences of a target nucleic acid molecule exhibiting genetic diversity. For example, when targeting. M gene of influenza A virus, all nucleic acid sequences known to the M gene are aligned and probes are designed being capable of covering all of these nucleic acid sequences. In this case, since a single probe cannot cover all M genes of various sequences, a plurality of probes (probes with different probing positions each other) are designed (see, FIG. 1).

The second method is to design a degenerate oligonucleotide. Typically, a conserved region is found in all nucleic acid sequences of a certain gene having genetic diversity, and the certain gene is detected with coverage of interest using a degenerate primer or probe (including a degenerate base at a variation site) that is hybridized with the conserved region (see, U.S. Pat. Nos. 8,735,063, 8,318,423, and 8,685,649).

For the first approach, it is most important to find an optimal combination of oligonucleotides used to detect various nucleic acid sequences of a target nucleic acid molecule with diversity. Taking into consideration convenience, efficiency and economy of an analysis, it is desirable to detect a target nucleic acid molecule with a desired coverage with a least oligonucleotide combination.

Conventionally, in order to detect nucleic acid sequences of a target nucleic acid molecule with genetic diversity, analysts have determined an optimal probe combination covering a plurality of nucleic acid sequences with sequentially or randomly preparing probe combinations for a plurality of nucleic acid sequences.

For example, assuming that there are six target nucleic acid sequences with diversity for a target nucleic acid molecule intended to detect and six probes covering the plurality of nucleic acid sequences as shown in FIG. 1, all combinations of probe 1 and probe 2, probe 1 and probe 3, and probe 2 and probe 3 can be manually made to provide probe 2 and probe 3 as the least probe combination covering all six sequences.

The conventional approach in which combinations of some of the plurality of probes are sequentially or randomly selected for determining to cover all sequences may be proposed when the number of target nucleic acid sequences and probes is small. However, where the number of target nucleic acid sequences and probes becomes much larger, or where a particular purpose such as detection with above a certain coverage and maximum target coverage with a limited number of probes is demanded, the conventional approach has serious shortcomings in light of the fact that it not only take a long time but also have poor accuracy.

To our best knowledge, there is no prior art that achieves the following technical purposes by using an optimization logic as the present invention: (i) preparing an oligonucleotide combination used to detect a plurality of target nucleic acid sequences with a target coverage of interest, (ii) selecting target nucleic acid sequences to be detected by a multiplex target detection with a highest target coverage by using a limited number of oligonucleotides, and (iii) determining a conserved region in a plurality of target nucleic acid sequences.

Throughout this application, various patents and publications are referenced and citations are provided in parentheses. The disclosure of these patents and publications in their entities are hereby incorporated by references into this application in order to more fully describe this invention and the state of the art to which this invention pertains.

SUMMARY OF THE INVENTION

The present inventor has made intensive researches to develop technologies for preparing an optimal combination of oligonucleotides covering a plurality of target nucleic acid sequences, inter alia, a plurality of nucleic acid sequences of a target nucleic acid molecule exhibiting genetic diversity (particularly, target nucleic acid sequences), with more improved speed and accuracy. As a result, the present inventor has developed optimization logic that finds an optimal combination of oligonucleotides hybridized with a plurality of target nucleic acid sequences, in a completely different approach from conventional methods, i.e., empirical and manual methods. In addition, the present inventor has found that the optimization logic may be used to (i) preparing an oligonucleotide combination used to detect a plurality of target nucleic acid sequences with a target coverage of interest, (ii) selecting target nucleic acid sequences to be detected by a multiplex target detection with a highest target coverage by using a limited number of oligonucleotides, and (iii) determining a conserved region in a plurality of target nucleic acid sequences.

Accordingly, it is an object of this invention to provide a method for preparing an oligonucleotide combination used to detect a plurality of target nucleic acid sequences with a target coverage of interest from a pool of oligonucleotides.

It is another object of this invention to provide a method for selecting target nucleic acid sequences to be detected by a multiplex target detection with a highest target coverage by using a limited number of oligonucleotides in a pool of oligonucleotides.

It is still another object of this invention to provide a method for determining a conserved region in a plurality of target nucleic acid sequences.

Other objects and advantages of the present invention will become apparent from the detailed description to follow taken in conjugation with the appended claims and drawings.

BRIEF DESCRIPTION OF THE DRAWINGS

FIG. 2 shows a binary matrix representing a non-coverage value and a coverage value indicating whether or not target nucleic acid sequences are covered by probes according to an embodiment of the present invention.

FIG. 3 exemplarily shows probes covering target nucleic acid sequences used in Examples to demonstrate that the present invention may provide an optimal probe combination.

FIG. 4 shows 10×10 binary matrix ($Y=\{y_{s,p}, y_{s,p}\in(0, 1)\}$) for a non-coverage value and a coverage value indicating whether or not the sequences 1 to 10 are covered by the probes 1 to 10 of FIG. 3.

DETAILED DESCRIPTION OF THIS INVENTION

Figure 1:
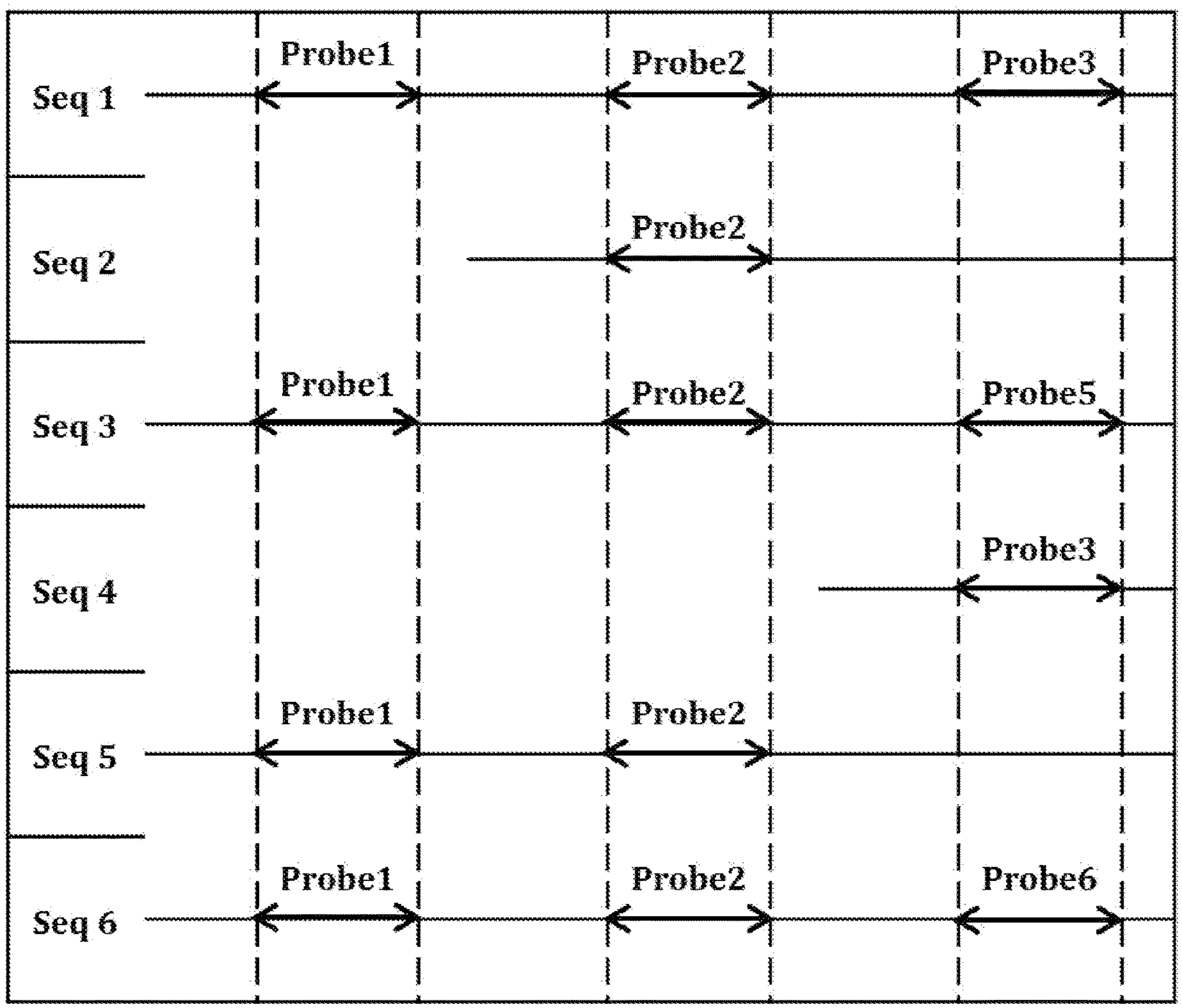
FIG. 1 shows probes 1 to 3, 5 and 6 covering six target nucleic acid sequences to schematically represent determination of an optimal probe combination according to a conventional method.

The technical purpose of the present invention is to efficiently make decisions that may be encountered by analysts in simultaneously detecting a plurality of target nucleic acid sequences, particularly a plurality of target nucleic acid sequences having sequence similarity, particularly (i) preparing an oligonucleotide combination used to detect a plurality of target nucleic acid sequences with a target coverage of interest, (ii) selecting target nucleic acid sequences to be detected by a multiplex target detection with a highest target coverage by using a limited number of oligonucleotides, and (iii) determining a conserved region in a plurality of target nucleic acid sequences.

The inventors have developed three most ideal optimization logics for these decisions. These logics share common features and therefore the present invention is largely divided into three aspects. Hereinafter, the present invention will be described in detail.

I. Preparation of Oligonucleotide Combination to Detect a Plurality of Target Nucleic Acid Sequences with Target Coverage of Interest In one aspect of the present invention, there is provided a method for preparing an oligonucleotide combination used to detect a plurality of target nucleic acid sequences with a target coverage of interest from a pool of oligonucleotides, comprising: (a) preparing the plurality of target nucleic acid sequences; (b) preparing the pool of oligonucleotides to be hybridized with the plurality of target nucleic acid sequences; and (c) selecting from the pool of oligonucleotides a least oligonucleotide combination with the target coverage of interest for the plurality of target nucleic acid sequences; wherein the selection of the least oligonucleotide combination is performed to achieve the following objective formula 1 together with satisfying the following constraint formulas 1 and 2, or the constraint formula 2:

$$\text{Min:}\sum_{p=1}^{a} x_p \qquad \text{Objective formula 1}$$

wherein Min: represents minimization, $x_p$ is a binary variable consisting of a non-selection value ($x_{non\text{-}sel}$) and a selection value ($x_{sel}$) for whether or not an oligonucleotide p is selected, and p is a serial number of the oligonucleotide p ranging from 1 to a;

$$\sum_{s=1}^{b} c_s \geq m \times S \qquad \text{Constraint formula 1}$$

wherein $c_s$ is a binary variable consisting of a non-coverage value ($c_{non\text{-}cov}$) and a coverage value ($c_{cov}$) for whether or not a target nucleic acid sequence s is covered, m is a target coverage of interest with a value of $0<m<1$, S is the total number of the plurality of target nucleic acid sequences, and s is a serial number of a target nucleic acid sequence s ranging from 1 to b;

$$\sum_{p=1}^{a} y_{s,p}x_p \geq c_s \text{ for all } s \qquad \text{Constraint formula 2}$$

wherein $y_{s,p}$ is a binary constant consisting of a non-coverage value ($y_{non\text{-}cov}$) and a coverage value ($y_{cov}$) representing whether or not a target nucleic acid sequence s is covered by an oligonucleotide p; $x_p$ is a binary variable for whether or not an oligonucleotide p is selected; $c_s$ is a binary variable for whether or not a target nucleic acid sequence s is covered in which $c_s$ is a coverage value ($c_{cov}$) when the target coverage of interest is 100% and $c_s$ is a non-coverage value ($c_{non\text{-}cov}$) and a coverage value ($c_{cov}$) when the target coverage of interest is less than 100%; and for all s represents application to all of target nucleic acid sequences s.

A first aspect of the present invention relates to a method for preparing an optimal combination of oligonucleotides (e.g., probes and primers) used to detect a plurality of target nucleic acid sequences with a target coverage of interest (e.g., 100% target coverage).

The term "detection with a target coverage of interest" used herein with referring to target nucleic acid sequences means detecting a plurality of target nucleic acid sequences that are capable of achieving a target coverage of interest, i.e., with a target coverage greater than or equal to a target coverage of interest.

The present invention will be described in more detail as follows:

Step (a): Preparing the Plurality of Target Nucleic Acid Sequences

First, the plurality of target nucleic acid sequences are prepared. The plurality of target nucleic acid sequences are used to construct a pool of oligonucleotides in the step (b), and are considered when determining an optimal combination of a pool of oligonucleotides in the step (c).

The term used herein "target nucleic acid molecule", "target molecule" or "target nucleic acid" means a nucleotide molecule in an organism intended to detect. Generally, the target nucleic acid molecule has a certain name and includes an entire genome and all nucleotide molecules that make up a genome (e.g., gene, pseudo gene, non-coding sequence molecule, untranslated region and some regions of genome).

The target nucleic acid molecule includes, for example, prokaryotic cell (e.g., *Mycoplasma pneumoniae, Chlamydophila pneumoniae, Legionella pneumophila, Haemophilus influenzae, Streptococcus pneumoniae, Bordetella pertussis, Bordetella parapertussis, Neisseria meningitidis, Listeria monocytogenes, Streptococcus agalactiae, Campylobacter, Clostridium difficile, Clostridium perfringens, Salmonella, Escherichia coli; Shigella, Vibrio, Yersinia enterocolitica, Aeromonas, Chlamydia trachomatis, Neisseria gonorrhoeae, Trichomonas vaginalis, Mycoplasma hominis, Mycoplasma genitalium, Ureaplasma urealyticum, Ureaplasma parvum, Mycobacterium tuberculosis*) nucleic acid, eukaryotic cell (e.g., protozoan and parasitic animal, fungus, yeast, higher plant, lower animal, and higher animal including mammal and human) nucleic acid, virus nucleic acid or viroid nucleic acid. Parasite of the eukaryotic cell includes, for example, *Giardia lamblia, Entamoeba histolytica, Cryptosporidium, Blastocystis hominis, Dientamoeba fragilis, Cyclospora cayetanensis*. Example of such virus includes influenza A virus (Flu A), influenza B virus (Flu B), respiratory syncytial virus A (RSV A), respiratory syncytial virus B (RSV B), parainfluenza virus 1 (PIV 1), parainfluenza virus 2 (PIV 2), parainfluenza virus 3 (PIV 3), parainfluenza virus 4 (PIV 4), metapneumovirus (MPV), human enterovirus (HEV), human bocavirus (HBoV), human rhinovirus (HRV), coronavirus and adenovirus, which cause respiratory diseases; norovirus, rotavirus, adenovirus, astrovirus, and sapovirus, which cause gastrointestinal disorders. The virus also includes, for example, human papillomavirus (HPV), middle east respiratory syndrome-related coronavirus (MERS-CoV), dengue virus, herpes simplex virus (HSV), human herpes virus (HHV), epstein-barr virus (EMV), varicella zoster virus (VZV), cytomegalovirus (CMV), HIV, hepatitis virus and poliovirus.

The term used herein "target nucleic acid sequence" or "target sequence" is to a certain sequence of a target nucleic acid molecule.

One target nucleic acid molecule, e.g., one target gene, may have a certain target nucleic acid sequence; otherwise for a target nucleic acid molecule exhibiting genetic diversity or genetic variability, it may have a plurality of target nucleic acid sequences with diversity. When it is intended to detect a target nucleic acid molecule exhibiting genetic diversity without a false negative result, a plurality of oligonucleotides being capable of covering a plurality of target nucleic acid sequences with diversity are usually required.

According to an embodiment of the present invention, the plurality of target nucleic acid sequences are target nucleic acid sequences having sequence similarity. Particularly, the target nucleic acid sequences having sequence similarity may be a plurality of target nucleic acid sequences of one target nucleic acid molecule or a plurality of target nucleic acid sequences of two or more target nucleic acid molecules.

According to an embodiment, the plurality of target nucleic acid sequences in the present invention are a plurality of nucleic acid sequences having sequence similarity for one target nucleic acid molecule having genetic diversity.

For example, the plurality of target nucleic acid sequences used in the present invention are a plurality of nucleic acid sequences having sequence similarity for a target nucleic acid molecule that exhibits genetic diversity such as a viral genome sequence. For example, when influenza A virus is intended to detect and the M gene is determined as a target nucleic acid molecule, target nucleic acid sequences with diversity of the M gene of influenza A virus may be used. Influenza A virus includes a variety of subtypes and variants, and their genomic sequences are different from each other. Therefore, when influenza A virus is intended to detect without a false negative result, an oligonucleotide should be designed considering various target nucleic acid sequences of a target nucleic acid molecule of influenza A virus originated from such genetic diversity.

More particularly, the plurality of target nucleic acid sequences are a whole genome sequence, a partial sequence of a genome, or a plurality of nucleic acid sequences of one gene of virus or bacteria having genetic diversity.

According to an embodiment of the present invention, the plurality of target nucleic acid sequences are a plurality of nucleic acid sequences from a plurality of organisms corresponding to homologues having the same function, the same structure, or the same gene name. The organism refers to an organism belonging to one genus, species, subspecies, subtype, genotype, serotype, strain, isolate or cultivar. The homologues include proteins and nucleic acid molecules. In this embodiment, a plurality of nucleic acid sequences of homologous biomolecules (e.g., protein or nucleic acid) of a plurality of organisms having the same function (e.g., a biological function of a protein encoded by a nucleic acid sequence), the same structure (e.g., a tertiary structure of a protein encoded by a nucleic acid sequence) or the same gene name are used. For example, a plurality of nucleic acid sequences known for the E5 gene of HPV type 16 may be considered as a nucleic acid sequence of isolates of HPV type 16. When the E5 gene is used as a target nucleic acid molecule for detecting HPV type 16, a plurality of oligonucleotides capable of covering a plurality of nucleic acid sequences with diversity of the E5 gene of HPV type 16 should be designed.

According to one embodiment, the target nucleic acid sequence comprises nucleic acid sequences belonging to a subclass of any biological classification (e.g., genus, species, subtype, genotype, serotype and subspecies) (for example, when the target nucleic acid sequence is HPV type 16, the target nucleic acid sequence may comprise nucleic acid sequences belonging to that subclass).

According to an embodiment of the present invention, the plurality of target nucleic acid sequences are at least 3, at least 5, at least 10, at least 20, at least 30, at least 40, at least 50, at least 60, at least 70, at least 80, at least 90 or at least 100 nucleic acid sequences.

A plurality of target nucleic acid sequences may be provided using various sequence databases. For example, a plurality of desired target nucleic acid sequences may be collected and provided from a publicly accessible database such as GenBank, European Molecular Biology Laboratory (EMBL) sequence database, and DNA DataBank of Japan (DDBJ).

According to an embodiment, a plurality of target nucleic acid sequences are aligned prior to the step (b). Alignment of target nucleic acid sequences may be performed according to various methods known in the art, which are described in detail below.

According to an embodiment of the present invention, the plurality of target nucleic acid sequences each has a unique serial number.

Step (b): Preparing the Pool of Oligonucleotides to be Hybridized with the Plurality of Target Nucleic Acid Sequences Then, the pool of oligonucleotides to be hybridized with the plurality of target nucleic acid sequences is prepared.

The prepared oligonucleotide pool is hybridized with the target nucleic acid sequence. The term used herein "hybridization" means forming a double-stranded nucleic acid from a complementary single-stranded nucleic acid. An oligonucleotide to be hybridized with a target nucleic acid sequence includes not only sequence that is perfectly complementary to a target nucleic acid sequence but also sequence that is enough to be specifically hybridized with a target nucleic acid sequence under certain stringent conditions. For example, an oligonucleotide may comprise one or more non-complementary nucleotides (i.e., mismatches) to a target nucleic acid sequence, as long as its specificity is not impaired. Therefore, in the present invention, an oligonucleotide may comprise a partially complementary and a perfectly complementary sequence to a target nucleic acid sequence, and particularly includes a perfectly complementary sequence (or a matching sequence).

A pool of oligonucleotides may be constructed for a whole genome sequence, a partial sequence of a genome, or a partial or entire sequence of one gene sequence as a target nucleic acid sequence. For example, where a target nucleic acid molecule is an entire genomic sequence of *Mycobacterium tuberculosis*, a plurality of genomic sequences with diversity of *Mycobacterium tuberculosis* are collected and aligned, and then oligonucleotides may be designed for the entire genome sequence or only conserved regions to prepare a pool of oligonucleotides.

According to an embodiment of the present invention, the pool of oligonucleotides comprises oligonucleotides that are hybridized with at least one sequence of the plurality of target nucleic acid sequences, and the oligonucleotides in the pool of oligonucleotides differ in a hybridization region and/or length from each other. Particularly, the pool of oligonucleotides includes a plurality of oligonucleotides that are hybridized with each of the plurality of target nucleic acid sequences, and is prepared with different hybridization region and/or length of the plurality of oligonucleotides.

According to an embodiment, the oligonucleotide is a probe and/or a primer. The term used herein "probe" refers to a single-stranded nucleic acid molecule comprising a portion or portions that are substantially complementary to a target nucleic acid sequence. The term "primer" as used herein refers to an oligonucleotide, which is capable of acting as a point of initiation of synthesis when placed under conditions in which synthesis of primer extension product which is complementary to a target nucleic acid sequence is induced, i.e., in the presence of nucleotides and an agent for polymerization, such as DNA polymerase, and at a suitable temperature and pH.

The oligonucleotides used in the present invention may have conventional primer and probe structure consisted of sequences that are hybridized with a target nucleic acid sequence. Alternatively, the oligonucleotide used in the present invention may have a unique structure. For example, the oligonucleotides used in the present invention may have a structure of Scorpion primer, Molecular beacon probe, Sunrise primer, HyBeacon probe, tagging probe, DPO primer or probe (WO 2006/095981), and PTO probe (WO 2012/096523).

The oligonucleotides used in the present invention may be a conventional primer or probe, or a modified oligonucleotide such as a degenerate base-containing oligonucleotide and/or a universal base-containing oligonucleotide. The term used herein "conventional primer", "conventional probe", and "conventional oligonucleotide" refer to a common primer, probe, and oligonucleotide into which a degeneate base or non-natural base is not introduced. According to an embodiment, when a degenerate base-containing oligonucleotide or a universal base-containing oligonucleotide is used in the present invention, at least 50%, at least 60%, at least 70%, at least 80%, at least 90% or at least 95% of the pool of oligonucleotides are non-modified oligonucleotide. The degenerate base includes the various degenerate bases known in the art as follows: R: A or G; Y: C or T; S: G or C; W: A or T; K: G or T; M: A or C; B: C or G or T; D: A or G or T; H: A or C or T; V: A or C or G; N: A or C or G or T. The universal base includes the following various universal bases known in the art: deoxyinosine, inosine, 7-deaza-2'-deoxyinosine, 2-aza-2'-deoxyinosine, 2'-0Me inosine, 2'-F inosine, deoxy 3-nitropyrrole, 3-nitropyrrole, 2'-0Me 3-nitropyrrole, 2'-F 3-nitropyrrole, 1-(2'-deoxy-beta-D-ribofuranosyl)-3-nitropyrrole, deoxy 5-nitropyrrole, 5-nitroindole, 2'-0Me 5-nitroindole, 2'-F 5-nitroindole, deoxy 4-nitrobenzimidazole, 4-nitrobenzimidazole, deoxy 4-aminobenzimidazole, 4-aminobenzimidazole, deoxy nebularine, 2'-F nebularine, 2'-F 4-nitrobenzimidazole, PNA-5-introindole, PNA-nebularine, PNA-inosine, PNA-4-nitrobenzimidazole, PNA-3-nitropyrrole, morpholino-5-nitroindole, morpholino-nebularine, morpholino-inosine, morpholino-4-nitrobenzimidazole, morpholino-3-nitropyrrole, phosphoramidate-5-nitroindole, phosphoramidate-nebularine, phosphoramidate-inosine, phosphoramidate-4-nitrobenzimidazole, phosphoramidate-3-nitropyrrole, 2'-O-methoxyethyl inosine, 2'O-methoxyethyl nebularine, 2'-O-methoxyethyl 5-nitroindole, 2'-O-methoxyethyl 4-nitrobenzimidazole, 2'-O-methoxyethyl 3-nitropyrrole, and combinations thereof. More particularly, the universal base is deoxyinosine, inosine, or combinations thereof.

The oligonucleotides used in the present invention may be probes or primers that satisfies the criteria to include a sequence to be hybridized with a target nucleic acid sequence or that satisfies at least one of the following additional criteria: (i) a $T_m$ value of 35° C. to 85° C.; (ii) a length of 15-50 nucleotides; (iii) a nucleotide sequence with 30-80% GC content; (iv) ΔG value in which the oligonucleotide forms a hairpin structure is −8.0 kcal/mol or more; (v) when the tagging oligonucleotide forms a homodimer, the ratio of nucleotides involved in the formation of the homodimer is 70% or less; (vi) when the oligonucleotide forms a homodimer, the ratio of consecutive nucleotides involved in the formation of the homodimer is 65% or less; (vii) when the oligonucleotide forms a heterodimer with another oligonucleotide, the ratio of nucleotides involved in the formation of the heterodimer is 70% or less; and (viii) when the oligonucleotide forms a heterodimer with another oligonucleotide, the ratio of consecutive nucleotides involved in the formation of the heterodimer is 65% or less.

According to an embodiment of the present invention, the oligonucleotides included in the pool of oligonucleotides each have a unique serial number.

Step (c): Selecting a Least Oligonucleotide Combination with the Target Coverage of Interest A least oligonucleotide combination with the target coverage of interest for the plurality of target nucleic acid sequences is selected from the pool of oligonucleotides.

The term used herein "target coverage" refers to a value indicating the degree to which the combination of the selected oligonucleotides is specifically hybridized with the plurality of target nucleic acid sequences. Particularly, the term "target coverage" means the ratio of target nucleic acid sequences to the plurality of target nucleic acid sequences with which the combination of the selected oligonucleotides is hybridized with substantial complementarity (particularly, with perfect complementarity or with perfect match). The target coverage may be expressed as the ratio or percentage. The term "interest" used herein with referring to target coverage may be used interchangeably with "desired" or "predetermined".

For example, where oligonucleotides are selected to cover three or more target nucleic acid sequences among the plurality of target nucleic acid sequences 1 to 6 of FIG. 1, the target coverage of interest is 0.5 or more (or 50% or more). For example, when oligonucleotides 2 and 3 are combined, the oligonucleotide 2 covers other sequences other than sequence 4, and the oligonucleotide 3 covers sequence 1 and 4 and does not other sequences. In this case, the ratio of the target nucleic acid sequence covered by such a combination is 100%. If the target coverage of interest is 100%, it may be achieved by the combination of oligonucleotides 2 and 3.

In the step (c), a least oligonucleotide combination with the target coverage of interest is found. The term "with a target coverage of interest" used herein with referring to oligonucleotides means oligonucleotides that are capable of showing a target coverage of interest, i.e., with a target coverage greater than or equal to a target coverage of interest. For example, 90% target coverage of interest indicates detecting target nucleic acid sequences with the target coverage of 90% or more using an oligonucleotide combination.

According to an embodiment of the present invention, the oligonucleotide selected from the pool of oligonucleotides may be a combination of primers, a combination of probes, or a combination of primers and probes. Particularly, the oligonucleotide selected from the pool of oligonucleotides is a combination of probes.

According to an embodiment, the oligonucleotide selected from the pool of oligonucleotides may be a combination of conventional oligonucleotides, a combination of at least one conventional oligonucleotide and at least one modified oligonucleotide, or a combination of at least two modified oligonucleotides.

According to an embodiment of the present invention, the modified oligonucleotide used in the present invention may be provided by introducing a degenerate base or universal base into at least one oligonucleotide of the selected oligonucleotides, when the number of oligonucleotides selected in the step (c) is large.

The most prominent feature of the present invention is the application of linear programming as optimization logic to select a least oligonucleotide combination that is used to detect a plurality of target nucleic acid sequences with a target coverage of interest.

The "linear programming" used in the present invention is an optimization technique that maximizes or minimizes a linear objective function while satisfying a given linear constraint formula (including constraint formula of non-negative number of a variable, a variable ≥0). Linear programming uses mathematical models to express problems, and both objective and constraint formulas are linear forms (i.e., linear function).

The selection of the least oligonucleotide combination is performed to achieve the following objective formula 1 together with satisfying the following constraint formulas 1 and 2, or the constraint formula 2:

$$\text{Min: } \sum_{p=1}^{a} x_p \qquad \text{Objective formula 1}$$

In the objective formula 1, Min: represents minimization, $x_p$ is a binary variable consisting of a non-selection value ($x_{non\text{-}sel}$) and a selection value ($x_{sel}$) for whether or not an oligonucleotide p is selected, and p is a serial number of the oligonucleotide p ranging from 1 to a.

$x_p$ is a decision variable and a binary variable for whether or not an oligonucleotide p is selected. With respect to the decision variable $x_p$, when an oligonucleotide p is not selected, it is indicated as a non-selection value ($x_{non\text{-}sel}$), and when an oligonucleotide p is selected, it is indicated as a selection value ($x_{sel}$). Particularly, the non-selection value ($x_{non\text{-}sel}$) is 0 and the selection value ($x_{sel}$) is a value other than 0. More particularly, the non-selection value ($x_{non\text{-}sel}$) and the selection value ($x_{sel}$) of $x_p$ are 0 and 1, respectively.

Since the method of the present invention selects a least oligonucleotide combination, the sum of a non-selection value ($x_{non\text{-}sel}$) and a selection value ($x_{sel}$) of a decision variable $x_p$ for an oligonucleotide of a serial number 1 to a is an objective function, and the minimization of the objective function becomes the objective formula 1.

The serial number of the oligonucleotide p is given to oligonucleotides of a pool of oligonucleotides, and the serial number a of the oligonucleotide p in the objective formula 1 is a serial number of the last oligonucleotide in the pool of oligonucleotides (particularly, an integer greater than 1).

According to the present invention, in order to select the least oligonucleotide combination, the following constraint formulas 1 and 2, or the constraint formula 2 should be satisfied:

$$\sum_{s=1}^{b} c_s \geq m \times S \qquad \text{Constraint formula 1}$$

In the constraint formula 1, $c_s$ is a binary variable consisting of a non-coverage value ($c_{non\text{-}cov}$) and a coverage value ($c_{cov}$) for whether or not a target nucleic acid sequence s is covered, m is a target coverage of interest with a value of 0<m<1, S is the total number of the plurality of target nucleic acid sequences, and s is a serial number of a target nucleic acid sequence s ranging from 1 to b.

In the present invention, $c_s$ is a decision variable and a binary variable for whether or not a target nucleic acid sequence s is covered. In the present invention, when the decision variable $c_s$ is expressed, it is indicated as a non-coverage value ($c_{non\text{-}cov}$) when a target nucleic acid sequence s is not covered, and as a coverage value ($c_{cov}$)

when a target nucleic acid sequence s is covered. Particularly, the non-coverage value ($c_{non\text{-}cov}$) is 0 and the coverage value ($c_{cov}$) is a value other than 0. More particularly, the non-coverage value ($c_{non\text{-}cov}$) and the coverage value ($c_{cov}$) of $c_s$ are 0 and 1, respectively.

The term "coverage" is used herein to mean that an oligonucleotide (a primer or a probe) is sufficiently complementary to be selectively hybridized with a target nucleic acid sequence under the designated annealing conditions or stringent conditions, encompassing the terms "substantially complementary" and "perfectly complementary", particularly perfectly complementary.

The $c_s$ is a decision variable for whether or not a target nucleic acid sequence s is covered and may have a non-coverage value ($c_{non\text{-}cov}$) in relation to a constraint formula even though an oligonucleotide p covers a target nucleic acid sequence s on a sequence. For example, where oligonucleotides 1 and 2 are combined, the oligonucleotide 1 covers a target nucleic acid sequence s and the oligonucleotide 2 does not cover the target nucleic acid sequence s, or although oligonucleotides 1 and 2 all cover the target nucleic acid sequence s, they may be considered not to cover the target nucleic acid sequence s in relation to a constraint formula. That is, in this case, the decision variable $c_s$ may be expressed as the non-coverage value ($c_{non\text{-}cov}$).

In the constraint formula 1, the target coverage of interest (m) is a target coverage intended to achieve by an experimenter and has a value of $0<m<1$. The selected oligonucleotides must satisfy this target coverage of interest.

In the constraint formula 1, S is the total number of the plurality of target nucleic acid sequences, and s is a serial number of the target nucleic acid sequence ranging from 1 to b. The serial number b (particularly, an integer greater than 1) of the target nucleic acid sequence s is equal to the total number of the plurality of target nucleic acid sequences, since b among the serial numbers of the target nucleic acid sequence s is the serial number of the last target nucleic acid sequence s. On the other hand, in FIG. 1, since there are six target nucleic acid sequences in total, S is 6 and the serial number b of the target nucleic acid sequence s is 6. Where the target coverage of interest is 0.5, $m \times S$ in the constraint formula 1 is 3. In the constraint formula 1, $m \times S$ is an integer.

The left side of the constraint formula 1 is the sum of the decision variable $c_s$ of the serial numbers 1 to b of a target nucleic acid sequence. For example, where the target nucleic acid sequence s has a serial number ranging from 1 to 6 (i.e., the total number of target nucleic acid sequences S=6) and the target coverage of interest is 0.83, the constraint formula 1 is $c_1+c_2+c_3+c_4+c_5+c_6 \geq 0.83 \times 6$.

$$\sum_{p=1}^{a} y_{s,p} x_p \geq c_s \text{ for all } s \qquad \text{Constraint formula 2}$$

In the constraint formula 2, $y_{s,p}$ is a binary constant consisting of a non-coverage value ($y_{non\text{-}cov}$) and a coverage value ($y_{cov}$) representing whether or not a target nucleic acid sequence s is covered by an oligonucleotide p, $x_p$ is a binary variable for whether or not an oligonucleotide p is selected; $c_s$ is a binary variable for whether or not a target nucleic acid sequence s is covered in which $c_s$ is a coverage value ($c_{cov}$) when the target coverage of interest is 100% and $c_s$ is a non-coverage value ($c_{non\text{-}cov}$) and a coverage value ($c_{cov}$) when the target coverage of interest is less than 100%; and for all s represents application to all of target nucleic acid sequences s.

The $y_{s,p}$ is a binary constant determined by whether or not a target nucleic acid sequence s is covered by an oligonucleotide p, i.e., by the given oligonucleotide and target nucleic acid sequence. When the $y_{s,p}$ is expressed, if an oligonucleotide p does not cover a target nucleic acid sequence s or an oligonucleotide p is non-complementary to a target nucleic acid sequence s, $y_{s,p}$ has a non-coverage value ($y_{non\text{-}cov}$), and when an oligonucleotide p covers a target nucleic acid sequence s or an oligonucleotide p is complementary to a target nucleic acid sequence s, $y_{s,p}$ has a coverage value ($y_{cov}$). Particularly, the non-coverage value ($y_{non\text{-}cov}$) is 0 and the coverage value ($y_{cov}$) is a value other than 0. More particularly, the non-coverage value ($y_{non\text{-}cov}$) and the coverage value ($y_{cov}$) of the $y_{s,p}$ are 0 and 1, respectively.

Since $x_p$ in the constraint formula 2 is the same as $x_p$ described in the objective formula 1, the common descriptions between them are omitted in order to avoid undue redundancy leading to the complexity of this specification.

In the constraint formula 2, $y_{s,p}x_p$ is a binary variable indicating whether a target nucleic acid sequence s is covered by a oligonucleotide p and whether the oligonucleotide p is selected, and a product of the binary constant for whether or not a target nucleic acid sequence s is covered by an oligonucleotide p and the binary variable for whether or not the oligonucleotide p is selected. Particularly, $y_{s,p}x_p$ may be expressed as a product of a non-coverage value ($y_{non\text{-}cov}$) and a non-selection value ($x_{non\text{-}sel}$), a product of a non-coverage value ($y_{non\text{-}cov}$) and a selection value ($x_{sel}$), a product of a coverage value ($y_{cov}$) and a non-selection value ($x_{non\text{-}sel}$), and a product of a coverage value ($y_{cov}$) and a selection value ($x_{sel}$). More particularly, when the non-coverage value ($y_{non\text{-}cov}$) and the non-selection value ($x_{non\text{-}sel}$) are represented by 0, and the coverage value ($y_{cov}$) and the selection value ($x_{sel}$) are represented by a value other than 0, the $y_{s,p}x_p$ may be indicated by 0 and a value other than 0. When the coverage value ($y_{cov}$) and the selection value ($x_{sel}$) are respectively represented by 1, the $y_{s,p}x_p$ may be indicated by 0 and 1.

Since the decision variable $c_s$ in the constraint formula 2 is the same as $c_s$ described in the constraint formula 1, the common descriptions between them are omitted in order to avoid undue redundancy leading to the complexity of this specification.

When it is intended to cover all target nucleic acid sequences by combining oligonucleotides (i.e., the target coverage of interest is 1 (100%)), $c_s$ in the constraint formula 2 has a coverage value ($c_{cov}$) for all target nucleic acid sequences. Particularly, the coverage value ($c_{cov}$) is a value other than 0, and more particularly, the coverage value ($c_{cov}$) is 1.

On the other hand, when it is desired to cover at least some of the target nucleic acid sequences by an oligonucleotide combination (i.e., the target coverage of interest is less than 1 (100%)), $c_s$ has the non-coverage value ($c_{non\text{-}cov}$) when the selected oligonucleotide does not cover the target nucleic acid sequences and the coverage value ($c_{cov}$) when covering at least one target nucleic acid sequence. Particularly, the non-coverage value ($c_{non\text{-}cov}$) is 0 and the coverage value ($c_{cov}$) is a value other than 0. More particularly, the non-coverage value ($c_{non\text{-}cov}$) and the coverage value ($c_{cov}$) of the $c_s$ are 0 and 1, respectively.

The constraint formula 2 is applied to all of the target nucleic acid sequence s. Particularly, the constraint formula 2 may be expressed for each serial number of the target nucleic acid sequence s. For example, when the serial number of the target nucleic acid sequence s ranges from 1 to 3 and the serial number of the oligonucleotide p ranges from 1 to 3, the constraint formula 2 is $y_{1,1}x_1+y_{1,2}x_2+y_{1,3}x_3 \geq c_1$, $y_{2,1}x_1+y_{2,2}x_2+y_{2,3}x_3 \geq c_2$ and $y_{3,1}x_1+y_{3,2}x_2+y_{3,3}x_3 \geq c_3$.

According to an embodiment of the present invention, the binary variable $c_s$ of the constraint formula 2 is $x_{a+s}$ in which a is the last serial number of an oligonucleotide p and s is a serial number of a target nucleic acid sequence s ranging from 1 to b. Particularly, since there is the binary variable $x_p$ on the left side of the constraint formula 2, $c_s$ may be replaced with $x_{a+s}$ to obtain an optimal solution by linear programming. For example, when the serial number of the oligonucleotide p ranges from 1 to 10 and the decision variable $c_s$ for the target nucleic acid sequence s having the serial number 1 is expressed, $c_1$ may be represented by $x_{10+1}$ or $x_{11}$.

According to an embodiment, the method is performed to achieve the objective formula 1 together with satisfying the constraint formulas 1 and 2 when the target coverage of interest is less than 100%, whereby the least oligonucleotide combination is selected and target nucleic acid sequences covered by the selected least oligonucleotide combination are selected among the plurality of target nucleic acid sequences. It is noteworthy that not only a least oligonucleotide combination, but also target nucleic acid sequences to be targeted, i.e., covered by a least oligonucleotide combination may be selected through one objective formula.

Where the method is performed to achieve the objective formula 1 together with satisfying the constraint formulas 1 and 2 when the target coverage of interest is less than 100%, the decision variables $x_p$ and $c_s$ may be obtained as solutions so that the least oligonucleotide combination may be selected and target nucleic acid sequences covered by the selected least oligonucleotide combination may be selected among the plurality of target nucleic acid sequences. For example, where the method is performed to achieve the objective formula 1 together with satisfying the constraint formulas 1 and 2 when the target coverage of interest is less than 100%, thereby obtaining $x_1=0$, $x_2=1$, $x_3=1$, $x_4=0$, $x_5=0$, $x_6=0$ and $c_1=1$, $c_2=1$, $c_3=1$, $c_4=0$, $c_5=1$, $c_6=1$ as solutions, the least oligonucleotide combination is a combination of oligonucleotides of the serial numbers 2 and 3, whereby the covered target nucleic acid sequences become the target nucleic acid sequences of the serial numbers 1 to 3, 5 and 6.

According to an embodiment of the present invention, the method is performed to achieve the objective formula 1 together with satisfying the constraint formula 2 when the target coverage of interest is 100%.

Where the method is performed to achieve the objective formula 1 together with satisfying the constraint formula 2 in case that the target coverage of interest is 100%, since all target nucleic acid sequences are covered, the decision variable $c_s$ for all the target nucleic acid sequences has a constant of a value other than 0 as the coverage value ($c_{cov}$), and particularly the $c_s$ is 1. In this case, the decision variable $x_p$ may be obtained as a solution, whereby selecting a least oligonucleotide combination. For example, where the method is performed to achieve the objective formula 1 together with satisfying the constraint formula 2 when the target coverage of interest is 100%, thereby obtaining $x_1=0$, $x_2=1$, $x_3=1$, $x_4=0$, $x_5=0$, $x_6=0$ as solutions, the least oligonucleotide combination is a combination of oligonucleotides of the serial numbers 2 and 3.

According to an embodiment, the method is preformed to achieve the following objective formula 1-1 together with satisfying the constraint formula 2, thereby selecting combinations of a limited number of oligonucleotides when target coverage of interest is 100%:

$$\sum_{p=1}^{a} x_p \leq X_{Lim}$$ Objective formula 1-1

In the objective formula 1-1, $x_p$ is a binary variable consisting of a non-selection value ($x_{non-sel}$) and a selection value ($x_{sel}$) for whether or not an oligonucleotide p is selected, p is a serial number of the oligonucleotide p ranging from 1 to a, and $X_{Lim}$ is a limited number of the oligonucleotide. Particularly, when a combination of a limited number of oligonucleotides covering all of a plurality of target nucleic acid sequences is selected, the method is preformed to achieve the objective formula 1-1 together with satisfying the constraint formula 2.

The method of the present invention is particularly useful when an oligonucleotide is designed to detect a plurality of pathogens with genetic diversity such as virus or to screen bacteria genus (e.g., *Campylobacter, Salmonella, Shigella, Vibrio, Aeromonas*).

II. Selection of Target Nucleic Acid Sequences to be Detected by a Mutiplex Target Detection with Highest Target Coverage by Using a Limited Number of Oligonucleotides In another aspect of this invention, there is provided a method for selecting target nucleic acid sequences to be detected by a multiplex target detection with a highest target coverage by using a limited number of oligonucleotides in a pool of oligonucleotides, comprising: (a) preparing a plurality of target nucleic acid sequences; (b) preparing the pool of oligonucleotides to be hybridized with the plurality of target nucleic acid sequences; and (c) selecting from the plurality of target nucleic acid sequences the target nucleic acid sequences to be detected; wherein the selection of the target nucleic acid sequences to be detected is performed to achieve the following objective formula 2 together with satisfying the following constraint formulas 3 and 2:

$$\text{Max: } \sum_{s=1}^{b} c_s$$ Objective formula 2 wherein Max: represents maximization, $c_s$ is a binary variable consisting of a non-coverage value ($c_{non-cov}$) and a coverage value ($c_{cov}$) for whether or not a target nucleic acid sequence s is covered, s is a serial number of a target nucleic acid sequence s ranging from 1 to b;

$$\sum_{p=1}^{a} x_p \leq X_{Lim}$$ Constraint formula 3 wherein $x_p$ is a binary variable consisting of a non-selection value ($x_{non-sel}$) and a selection value ($x_{sel}$) for whether or not an oligonucleotide p is selected, p is a serial number of the oligonucleotide p ranging from 1 to a, and $X_{Lim}$ is a limited number of the oligonucleotide;

$$\sum_{p=1}^{a} y_{s,p} x_p \geq c_s \text{ for all } s \quad \text{Constraint formula 2}$$

wherein $y_{s,p}$ is a binary constant consisting of a non-coverage value ($y_{non\text{-}cov}$) and a coverage value ($y_{cov}$) representing whether or not a target nucleic acid sequence s is covered by an oligonucleotide p; $x_p$ is a binary variable for whether or not an oligonucleotide p is selected; $c_s$ is a binary variable for whether or not a target nucleic acid sequence s is covered in which $c_s$ is a coverage value ($c_{cov}$) when the target coverage of interest is 100% and $c_s$ is a non-coverage value ($c_{non\text{-}cov}$) and a coverage value ($c_{cov}$) when the target coverage of interest is less than 100%; and for all s represents application to all of target nucleic acid sequences s.

A second aspect of the present invention relates to a method of selecting target nucleic acid sequences to be detected by a multiplex target detection (i.e., detection of a plurality of target nucleic acid sequences) with a highest target coverage by using a limited number of oligonucleotides in a pool of oligonucleotides. Because the second aspect of the present invention has the same binary variables $x_p$ and $c_s$, and binary constant $y_{s,p}$ as the first method except for the objective formula 2, the constraint formula 3, and a combination of the constraint formulas 3 and 2, the common descriptions between them are omitted in order to avoid undue redundancy leading to the complexity of this specification.

The second aspect of the present invention is an optimization method for maximizing target coverage for target nucleic acid sequences to be detected in which the number of oligonucleotides is given with a limited number.

The term "a limited number" used herein with referring to the number of oligonucleotides means to detect a plurality of target nucleic acid sequences with a highest target coverage by using a limited number or less of oligonucleotides. For example, a limited number of oligonucleotides of 3 indicate detecting a plurality of target nucleic acid sequences with a highest target coverage using a combination of three or less oligonucleotides.

The present invention will be described in more detail as follows:

Step (a): Preparing a Plurality of Target Nucleic Acid Sequences

First, a plurality of target nucleic acid sequences are prepared. The step (a) of the second method of the present invention may be described with reference to the description for the step (a) of the first method.

Step (b): Preparing the Pool of Oligonucleotides to be Hybridized with the Plurality of Target Nucleic Acid Sequences Then, the pool of oligonucleotides to be hybridized with the plurality of target nucleic acid sequences is prepared. The step (b) of the second method of the present invention may be described with reference to the description for the step (b) of the first method.

Step (c): Selecting from the Plurality of Target Nucleic Acid Sequences the Target Nucleic Acid Sequences to be Detected Afterwards, the target nucleic acid sequences to be detected are selected from the plurality of target nucleic acid sequences. The selection of the target nucleic acid sequences to be detected is performed to achieve the following objective formula 2 together with satisfying the following constraint formulas 3 and 2:

$$\text{Max: } \sum_{s=1}^{b} c_s \quad \text{Objective formula 2}$$

In the objective formula 2, Max: represents maximization, $c_s$ is a binary variable consisting of a non-coverage value ($c_{non\text{-}cov}$) and a coverage value ($c_{cov}$) for whether or not a target nucleic acid sequence s is covered, s is a serial number of a target nucleic acid sequence s ranging from 1 to b.

Since the second method of the present invention is to select target nucleic acid sequences to be detected by a multiplex target detection with a highest target coverage, the sum of binary variable $c_s$ is used as an objective function to maximize the sum.

In the objective formula 2, the binary variable $c_s$ may be described with reference to the description for the step (c) of the first method.

$$\sum_{p=1}^{a} x_p \leq X_{Lim} \quad \text{Constraint formula 3}$$

In the constraint formula 3, $x_p$ is a binary variable consisting of a non-selection value ($x_{non\text{-}sel}$) and a selection value ($x_{sel}$) for whether or not an oligonucleotide p is selected, p is a serial number of the oligonucleotide p ranging from 1 to a, and $X_{Lim}$ is a limited number of the oligonucleotide.

Since the second method of the present invention is required to utilize a limited number of oligonucleotides, a constraint formula may be defined as the constraint formula 3. In the constraint formula 3, the binary variable $x_p$ may be described with reference to the description for the step (c) of the first method. For example, when a combination of a highest of three oligonucleotides is used with a proviso that the serial number of an oligonucleotide p ranges from 1 to 6, the constraint formula 3 is $x_1+x_2+x_3+x_4+x_5+x_6 \leq 3$.

$$\sum_{p=1}^{a} y_{s,p} x_p \geq c_s \text{ for all } s \quad \text{Constraint formula 2}$$

In the constraint formula 2, $y_{s,p}$ is a binary constant consisting of a non-coverage value ($y_{non\text{-}cov}$) and a coverage value ($y_{cov}$) representing whether or not a target nucleic acid sequence s is covered by an oligonucleotide p; $x_p$ is a binary variable for whether or not an oligonucleotide p is selected; $c_s$ is a binary variable for whether or not a target nucleic acid sequence s is covered in which $c_s$ is a coverage value ($c_{cov}$) when the target coverage of interest is 100% and $c_s$ is a non-coverage value ($c_{non\text{-}cov}$) and a coverage value ($c_{cov}$) when the target coverage of interest is less than 100%; and for ails represents application to all of target nucleic acid sequences s.

The constraint formula 2 may be described with reference to the description for the step (c) of the first method.

According to an embodiment of the present invention, the target nucleic acid sequences to be detected are selected and a combination of the limited number of oligonucleotides to be hybridized with the selected target nucleic acid sequences is selected. It is noteworthy that not only the selection of target nucleic acid sequences to be detected but also the selection of a combination of the limited number of oligonucleotides used to the detection of the selected target nucleic acid sequences may be made by using one objective formula.

Particularly, where the method is performed to achieve the objective formula 2 together with satisfying the constraint formulas 3 and 2, the decision variables $x_p$ and $c_s$ may be obtained as solutions so that the selection of target nucleic acid sequences to be detected and the selection of the limited number of oligonucleotides hybridized with the selected target nucleic acid sequences may be achieved.

Ranking of Optimal Oligonucleotide Combinations

The method of the invention described above may provide more than one oligonucleotide combination. Where there are two or more oligonucleotide combinations, the oligonucleotides may be re-selected as follows: For example, when the three combinations including (i) oligonucleotides of serial numbers 1 and 2, (ii) oligonucleotides of serial numbers 7 and 9 and (iii) oligonucleotides of serial numbers 11 and 21 are prepared as combinations of oligonucleotides p that satisfy the constraint formulas and achieve the objective formula of the present invention described above, an optimal combination to be used for detection of a plurality of target nucleic acid sequences may be selected from the three combinations.

According to an embodiment, when two or more oligonucleotide combinations are selected, additional selection may be performed to select a more suitable oligonucleotide combination.

According to one embodiment of the present invention, the method further comprises assigning ranks to the combinations of the oligonucleotides in accordance with at least one of the following priority items:

(i) the target coverage for the plurality of target nucleic acid sequences; wherein the higher the target coverage, the higher the priority, (ii) when the oligonucleotide forms a homodimer, the number or proportion of consecutive nucleotides involved in the formation of the homodimer; wherein the smaller the number or proportion, the higher the priority, (iii) a hairpin structure-forming free energy value (ΔG value); wherein the higher the free energy value, the higher the priority, and (iv) a length; wherein the shorter the length, the higher the priority.

According to the present invention, the combinations of the oligonucleotides are ranked with regard to at least one (particularly, priority item (i)), particularly at least 2, more particularly at least 3, still more particularly at least 4 priority items.

According to an embodiment, the at least two priority items differ from each other in terms of criticality and the method further comprises selecting at least one combination of oligonucleotides in accordance with ranks in the at least two priority items with considering the criticality.

There are two methods for selecting a more suitable oligonucleotide combination:

According to the first method, the at least two priority items differ from each other in terms of criticality and a top-most oligonucleotide combination may be selected by ranking for the priority item having the highest criticality (e.g., priority item (i)). When a plurality of top-most oligonucleotide combinations are present in the priority item with the highest criticality, the oligonucleotide combination having the highest rank is selected by comparing ranks in a priority item with just lower criticality than the highest criticality. For example, if the criticality of the priority items is in the order of (i)-(iii) and there are 5 top-most oligonucleotide combinations in the priority item (i), the ranks of the 5 top-most oligonucleotide combinations is compared in the priority item (ii). If the ranks in the priority item (ii) are also the same, the oligonucleotide combination having the highest rank is selected by comparing ranks in the priority item (iii).

According to the second method, the total score of each oligonucleotide combination may be obtained by assigning different weights to priority items and assigning scores to values (or ranges of values) in each priority item. Taking this calculated total score into consideration, a more suitable oligonucleotide combination may be selected.

Where the detection of a plurality of target nucleic acid sequences is performed using an appropriate combination of a probe and a primer such as PTOCE (see, WO 2012/096523) and TaqMan methods, partnerships or collaboration between the probe and the primer in the detection of the target nucleic acid sequence are important although excellent characteristics of the probe and the primer itself are also important. For example, primers should be located upstream and downstream with regard to the selected probe, and be capable of forming an amplicon having an appropriate size (particularly, 100-1000, more particularly 200-800, still more particularly 300-700, still much more particularly 300-500, most particularly 300-400 nucleotides). Particularly, a primer should have no interference with a probe. A representative of such interference is dimer formation. Although the primer and the probe have excellent properties, the primer may not be appropriate when it forms a heterodimer with the probe. Particularly, a primer has a lower $T_m$ value than a probe. For example, the $T_m$ value of the primer may be in the range of [55° C. to ($T_m$ of the probe minus 10° C.) ° C.] in relation to the probe.

According to an embodiment, the prioritized oligonucleotide combinations are probe combinations, a top-most probe combination is selected from the prioritized probe combinations and primers suitable for the top-most probe are selected. The term "suitable" means possession of at least one of the following characteristics: with respect to the selected probe combination, a primer and the probe do not form a heterodimer, primers form an amplicon of the desired size, and a primer has a $T_m$ value of [55° C. to ($T_m$ of the probe minus 10° C.) ° C.].

For example, where probe combination and primers selected is provided by the present invention, a top-most probe combination is selected and top-most primers suitable for this probe combination are selected. If primers suitable for the top-most probe combination are absent, suitable primers are re-selected for a probe combination with just lower rank than the top-most probe combination. This primer combination and the probe combination with just lower rank than the top-most probe combination are used as oligonucleotides for detecting a plurality of target nucleic acid sequences.

III. Determination of Conserved Region in a Plurality of Target Nucleic Acid Sequences (Third Aspect)

A third aspect of the present invention is drawn to a method for determining a conserved region in a plurality of target nucleic acid sequences based on the first aspect.

In the third aspect of this invention, there is provided a method for determining a conserved region in a plurality of target nucleic acid sequences, comprising: (a) preparing the plurality of target nucleic acid sequences; (b) aligning the plurality of target nucleic acid sequences; (c) preparing the pool of oligonucleotides to be hybridized with the plurality of target nucleic acid sequences; (d) selecting from the pool of oligonucleotides a least oligonucleotide combination with a target coverage of interest for the plurality of target nucleic acid sequences; wherein the selection of the least oligonucleotide combination is performed to achieve the following objective formula 1 together with satisfying the following constraint formulas 1 and 2, or the constraint formula 2:

$$\text{Min: } \sum_{p=1}^{a} x_p \qquad \text{Objective formula 1}$$

wherein Min: represents minimization, $x_p$ is a binary variable consisting of a non-selection value ($x_{non\text{-}sel}$) and a selection value ($x_{sel}$) for whether or not an oligonucleotide p is selected, and p is a serial number of the oligonucleotide p ranging from 1 to a;

$$\sum_{s=1}^{b} c_s \geq m \times S \qquad \text{Constraint formula 1}$$

wherein $c_s$ is a binary variable consisting of a non-coverage value ($c_{non\text{-}cov}$) and a coverage value ($c_{cov}$) for whether or not a target nucleic acid sequence s is covered, m is a target coverage of interest with a value of 0<m<1, S is the total number of the plurality of target nucleic acid sequences, and s is a serial number of a target nucleic acid sequence s ranging from 1 to b;

$$\sum_{p=1}^{a} y_{s,p} x_p \geq c_s \text{ for all } s \qquad \text{Constraint formula 2}$$

wherein $y_{s,p}$ is a binary constant consisting of a non-coverage value ($y_{non\text{-}cov}$) and a coverage value ($y_{cov}$) representing whether or not a target nucleic acid sequence s is covered by an oligonucleotide p; $x_p$ is a binary variable for whether or not an oligonucleotide p is selected; $c_s$ is a binary variable for whether or not a target nucleic acid sequence s is covered in which $c_s$ is a coverage value ($c_{cov}$) when the target coverage of interest is 100% and $c_s$ is a non-coverage value ($c_{non\text{-}cov}$) and a coverage value ($c_{cov}$) when the target coverage of interest is less than 100%; and for all s represents application to all of target nucleic acid sequences s; and (e) determining as the conserved region a region of the plurality of target nucleic acid sequences covered by the least oligonucleotide combination.

A conserved region which is a biologically very meaningful portion represents a portion where sequences are similar or identical in different nucleic acid molecules between different organisms from each other. The conserved region is used as a very important indicator for phylogenetic studies and is also used as a probing portion when different organisms are detected in a multiplex manner.

According to the present invention, conserved sequences between different organisms may be determined in a unique manner, and the conserved region comprising these conserved sequences may be used as the portion (i.e., probing region) with which a primer or a probe is hybridized.

The present invention is described as a method for determining a conserved region, but this may also be expressed as a method of determining a probing region. Where the least oligonucleotide combination exhibits target coverage of interest (e.g., 100%) for a plurality of target nucleic acid sequences in accordance with the invention described above, the probing portion of this least oligonucleotide combination may be presented as the conserved region.

Since the third aspect of the present invention is based on the first aspect of the present invention described above, the common descriptions between them are omitted in order to avoid undue redundancy leading to the complexity of this specification.

The present invention will be described in more detail as follows:

Step (a): Preparing the Plurality of Target Nucleic Acid Sequences

The step (a) of the third method of the present invention may be described with reference to the description for the step (a) of the first method.

Step (b): Aligning the Plurality of Target Nucleic Acid Sequences

Then, the plurality of target nucleic acid sequences are aligned.

Alignment may be performed according to various methods (e.g., global alignment and local alignment) and algorithms known in the art.

Various methods and algorithms for alignment are described in Smith and Waterman, *Adv. Appl. Math.* 2:482 (1981); Needleman and Wunsch, *J. Mol. Bio.* 48:443 (1970); Pearson and Lipman, *Methods in Mol. Biol.* 24: 307-31 (1988); Higgins and Sharp, *Gene* 73:237-44(1988); Higgins and Sharp, *CABIOS* 5:151-3(1989); Corpet et al., *Nuc. Acids Res.* 16: 10881-90 (1988); Huang et al., *Comp. Appl. BioSci.* 8:155-65(1992) and Pearson et al., *Meth. Mol. Biol.* 24:307-31(1994). The NCBI Basic Local Alignment Search Tool (BLAST) (Altschul et al., *J. Mol. Biol.* 215:403-10(1990)) is accessible from NCBI (National Center for Biological Information) and may be used in conjunction with sequence analysis programs such as blastn, blasm, blastx, tblastn and tblastx on the Internet. BLSAT is available at http://www.ncbi.nlm.nih.gov/BLAST/. A comparison of sequence similarity using this program may be found at http://www.ncbi.nlm.nih.gov/BLAST/blast_help.html.

Step (c): Preparing the Pool of Oligonucleotides to be Hybridized with the Plurality of Target Nucleic Acid Sequences Afterward, the pool of oligonucleotides to be hybridized with the plurality of target nucleic acid sequences is prepared, which may be described with reference to the description for the step (b) of the first method.

Step (d): Selecting a Least Oligonucleotide Combination with a Target Coverage of Interest A least oligonucleotide combination with a target coverage of interest for the plurality of target nucleic acid sequences is selected from the pool of oligonucleotides. The selection of the least oligonucleotide combination is performed to achieve the following objective formula 1 together with satisfying the following constraint formulas 1 and 2, or the constraint formula 2:

$$\text{Min: } \sum_{p=1}^{a} x_p \qquad \text{Objective formula 1}$$

In the objective formula 1, Min: represents minimization, $x_p$ is a binary variable consisting of a non-selection value ($x_{non-sel}$) and a selection value ($x_{sel}$) for whether or not an oligonucleotide p is selected, and p is a serial number of the oligonucleotide p ranging from 1 to a;

$$\sum_{s=1}^{b} c_s \geq m \times S \quad \text{Constraint formula 1}$$

In the constraint formula 1, $c_s$ is a binary variable consisting of a non-coverage value ($c_{non-cov}$) and a coverage value ($c_{cov}$) for whether or not a target nucleic acid sequence s is covered, m is a target coverage of interest with a value of 0<m<1, S is the total number of the plurality of target nucleic acid sequences, and s is a serial number of a target nucleic acid sequence s ranging from 1 to b;

$$\sum_{p=1}^{a} y_{s,p} x_p \geq c_s \text{ for all } s \quad \text{Constraint formula 2}$$

In the constraint formula 2, $y_{s,p}$ is a binary constant consisting of a non-coverage value ($y_{non-cov}$) and a coverage value ($y_{cov}$) representing whether or not a target nucleic acid sequence s is covered by an oligonucleotide p; $x_p$ is a binary variable for whether or not an oligonucleotide p is selected; $c_s$ is a binary variable for whether or not a target nucleic acid sequence s is covered in which $c_s$ is a coverage value ($c_{cov}$) when the target coverage of interest is 100% and $c_s$ is a non-coverage value ($c_{non-cov}$) and a coverage value ($c_{cov}$) when the target coverage of interest is less than 100%; and for all s represents application to all of target nucleic acid sequences s.

The least oligonucleotide combination selection of the step (d) may be described with reference to the description for the step (c) of the first aspect.

Step (e): Determining the Conserved Region

Finally, a region of the plurality of target nucleic acid sequences covered by the least oligonucleotide combination is determined as the conserved region.

When a plurality of target nucleic acid sequences (e.g., 80 target nucleic acid sequences) are 100% covered by a least oligonucleotide combination (e.g., two oligonucleotides), this means that a plurality of target nucleic acid sequences have a high sequence similarity and are highly conservative.

According to an embodiment of the present invention, among the least oligonucleotide combinations covering a plurality of target nucleic acid sequences, a region between the 5'-end of the most upstream oligonucleotide and the 3'-end of the most downstream oligonucleotide may be determined as the conserved region.

According to one embodiment, the distance between the 5'-end of the most upstream oligonucleotide and the 3'-end of the most downstream oligonucleotide is 40-1000 nucleotides, 60-500 nucleotides or 70-500 nucleotides.

According to an embodiment of the present invention, the least oligonucleotide combination particularly includes 2-10 oligonucleotides, 2-8 oligonucleotides, 2-6 oligonucleotides, 2-4 oligonucleotides, or 2-3 oligonucleotides.

According to an embodiment, the present invention evaluates the conserved region in consideration of both the target coverage of interest and the number of oligonucleotides included in the least oligonucleotide combination. For example, when the target coverage of interest is 100% and the number of oligonucleotides included in the least oligonucleotide combination is two, the determined conserved region may be considered as a highly conserved region. Thus, according to the present invention, it is allowed to distinguish whether the determined conserved region is a highly conserved region, a moderately conserved region or a low conserved region.

According to an embodiment of the present invention, the present invention after the step (b), further comprises designating a plurality of candidate conserved regions in the plurality of target nucleic acid sequences aligned. The designation of the candidate conserved region may be carried out by selecting regions having high sequence similarity according to conventional methods. In this case, the step (c) may be carried out by providing a pool of oligonucleotides that are hybridized with the plurality of candidate conserved regions rather than the entire sequences of the plurality of target nucleic acid sequences. The step (d) may also be carried out by selecting from the pool of oligonucleotides a least oligonucleotide combination with a target coverage of interest for each of the plurality of candidate conserved regions.

IV. Determination of Conserved Region in a Plurality of Target Nucleic Acid Sequences (Fourth Aspect)

A fourth method of the present invention relates to a method for determining a conserved region in a plurality of target nucleic acid sequences based on the second method of the present invention.

In another aspect of this invention, there is provided a method for determining a conserved region in a plurality of target nucleic acid sequences, comprising: (a) preparing the plurality of target nucleic acid sequences; (b) aligning the plurality of target nucleic acid sequences; (c) preparing the pool of oligonucleotides to be hybridized with the plurality of target nucleic acid sequences; (d) selecting from the plurality of target nucleic acid sequences target nucleic acid sequences to be detected with a highest target coverage by using a limited number of oligonucleotides; wherein the selection of the target nucleic acid sequences to be detected is performed to achieve the following objective formula 2 together with satisfying the following constraint formulas 3 and 2:

$$\text{Max: } \sum_{s=1}^{b} c_s \quad \text{Objective formula 2}$$

wherein Max: represents maximization, $c_s$ is a binary variable consisting of a non-coverage value ($c_{non-cov}$) and a coverage value ($c_{cov}$) for whether or not a target nucleic acid sequence s is covered, s is a serial number of a target nucleic acid sequence s ranging from 1 to b;

$$\sum_{p=1}^{a} x_p \leq X_{Lim} \quad \text{Constraint formula 3}$$

wherein $x_p$ is a binary variable consisting of a non-selection value ($x_{non-sel}$) and a selection value ($x_{sel}$) for whether or not an oligonucleotide p is selected, p is a serial number of the oligonucleotide p ranging from 1 to a, and $X_{Lim}$ is a limited number of the oligonucleotide;

$$\sum_{p=1}^{a} y_{s,p} x_p \geq c_s \text{ for all } s$$ Constraint formula 2 wherein $y_{s,p}$ is a binary constant consisting of a non-coverage value ($y_{non\text{-}cov}$) and a coverage value ($y_{cov}$) representing whether or not a target nucleic acid sequence s is covered by an oligonucleotide p; $x_p$ is a binary variable for whether or not an oligonucleotide p is selected; $c_s$ is a binary variable for whether or not a target nucleic acid sequence s is covered in which $c_s$ is a coverage value ($c_{cov}$) when the target coverage of interest is 100% and $c_s$ is a non-coverage value ($c_{non\text{-}cov}$) and a coverage value ($c_{cov}$) when the target coverage of interest is less than 100%; and for all s represents application to all of target nucleic acid sequences s; and (e) determining as the conserved region a region of the target nucleic acid sequences to be detected with the highest target coverage by the limited number of oligonucleotides.

Since the fourth method of the present invention is based on the second method of the present invention described above and determines the conserved region as the third method of the present invention described above, the common descriptions between them are omitted in order to avoid undue redundancy leading to the complexity of this specification.

In the step (e), among the target nucleic acid sequences finally selected in the step (d), a region of the target nucleic acid sequences covered with a highest target coverage by a limited number (particularly, the smallest number) of oligonucleotides is determined as the conserved region. For example, when up to 60 of 80 target nucleic acid sequences (the highest target coverage of 75%) are covered by two oligonucleotides as a limited number (particularly, the smallest number), the region of the target nucleic acid sequences covered by the two oligonucleotides is determined as the conserved region.

According to an embodiment of the present invention, the present invention after the step (b), further comprises designating a plurality of candidate conserved regions in the plurality of target nucleic acid sequences aligned. The designation of the candidate conserved region may be carried out by selecting regions having high sequence similarity according to conventional methods. In this case, the step (c) may be carried out by providing a pool of oligonucleotides that are hybridized with the plurality of candidate conserved regions rather than the entire sequences of the plurality of target nucleic acid sequences. In addition, the step (d) may be carried out by selecting target nucleic acid sequences detected with a highest target coverage by a limited number of oligonucleotides for each of the plurality of candidate conserved regions.

V. Storage Medium, Device and Program

In another aspect of this invention, there is provided a computer readable storage medium containing instructions to configure a processor to perform a method for preparing an oligonucleotide combination used to detect a plurality of target nucleic acid sequences with a target coverage of interest from a pool of oligonucleotides, the method comprising:

selecting from the pool of oligonucleotides a least oligonucleotide combination with the target coverage of interest for the plurality of target nucleic acid sequences; wherein the selection of the least oligonucleotide combination is performed to achieve the following objective formula 1 together with satisfying the following constraint formulas 1 and 2, or the constraint formula 2:

$$\text{Min: } \sum_{p=1}^{a} x_p$$ Objective formula 1 wherein Min: represents minimization, $x_p$ is a binary variable consisting of a non-selection value ($x_{non\text{-}sel}$) and a selection value ($x_{sel}$) for whether or not an oligonucleotide p is selected, and p is a serial number of the oligonucleotide p ranging from 1 to a;

$$\sum_{s=1}^{b} c_s \geq m \times S$$ Constraint formula 1 wherein $c_s$ is a binary variable consisting of a non-coverage value ($c_{non\text{-}cov}$) and a coverage value ($c_{cov}$) for whether or not a target nucleic acid sequence s is covered, m is a target coverage of interest with a value of 0<m<1, S is the total number of the plurality of target nucleic acid sequences, and s is a serial number of a target nucleic add sequence s ranging from 1 to b;

$$\sum_{p=1}^{a} y_{s,p} x_p \geq c_s \text{ for all } s$$ Constraint formula 2 wherein $y_{s,p}$ is a binary constant consisting of a non-coverage value ($y_{non\text{-}cov}$) and a coverage value ($y_{cov}$) representing whether or not a target nucleic add sequence s is covered by an oligonucleotide p; $x_p$ is a binary variable for whether or not an oligonucleotide p is selected; $c_s$ is a binary variable for whether or not a target nucleic acid sequence s is covered in which $c_s$ is a coverage value ($c_{cov}$) when the target coverage of interest is 100% and $c_s$ is a non-coverage value ($c_{non\text{-}cov}$) and a coverage value ($c_{cov}$) when the target coverage of interest is less than 100%; and for all s represents application to all of target nucleic acid sequences s.

In still another aspect of this invention, there is provided a computer program to be stored on a computer readable storage medium, to configure a processor to perform a method for preparing an oligonucleotide combination used to detect a plurality of target nucleic acid sequences with a target coverage of interest from a pool of oligonucleotides, and the method is the same as the method described in the computer readable storage medium described above.

In another aspect of this invention, there is provided a device for preparing an oligonucleotide combination used to detect a plurality of target nucleic acid sequences with a target coverage of interest from a pool of oligonucleotides, comprising (a) a computer processor, and (b) a computer readable storage medium of the present method coupled to the computer processor.

In another aspect of this invention, there is provided a computer readable storage medium containing instructions to configure a processor to perform a method for selecting target nucleic acid sequences to be detected by a multiplex target detection with a highest target coverage by using a limited number of oligonucleotides in a pool of oligonucleotides, the method comprising:

selecting from the plurality of target nucleic acid sequences the target nucleic acid sequences to be detected; wherein the selection of the target nucleic acid sequences to be detected is performed to achieve the following objective formula 2 together with satisfying the following constraint formulas 3 and 2:

$$\text{Max: } \sum_{s=1}^{b} c_s \quad \text{Objective formula 2}$$

wherein Max: represents maximization, $c_s$ is a binary variable consisting of a non-coverage value ($c_{non\text{-}cov}$) and a coverage value ($c_{cov}$) for whether or not a target nucleic acid sequence s is covered, s is a serial number of a target nucleic acid sequence s ranging from 1 to b;

$$\sum_{p=1}^{a} x_p \leq X_{Lim} \quad \text{Constraint formula 3}$$

wherein $x_p$ is a binary variable consisting of a non-selection value ($x_{non\text{-}sel}$) and a selection value ($x_{sel}$) for whether or not an oligonucleotide p is selected, p is a serial number of the oligonucleotide p ranging from 1 to a, and $X_{Lim}$ is a limited number of the oligonucleotide;

$$\sum_{p=1}^{a} y_{s,p} x_p \geq c_s \text{ for all } s \quad \text{Constraint formula 2}$$

wherein $y_{s,p}$ is a binary constant consisting of a non-coverage value ($y_{non\text{-}cov}$) and a coverage value ($y_{cov}$) representing whether or not a target nucleic acid sequence s is covered by an oligonucleotide p; $x_p$ is a binary variable for whether or not an oligonucleotide p is selected; $c_s$ is a binary variable for whether or not a target nucleic acid sequence s is covered in which $c_s$ is a coverage value ($c_{cov}$) when the target coverage of interest is 100% and $c_s$ is a non-coverage value ($c_{non\text{-}cov}$) and a coverage value ($c_{cov}$) when the target coverage of interest is less than 100%; and for all s represents application to all of target nucleic acid sequences s.

In still another aspect of this invention, there is provided a computer program to be stored on a computer readable storage medium, to configure a processor to perform a method for selecting target nucleic acid sequences to be detected by a multiplex target detection with a highest target coverage by using a limited number of oligonucleotides in a pool of oligonucleotides, and the method is the same as the method described in the computer readable storage medium described above.

In still another aspect of this invention, there is provided a device for selecting target nucleic acid sequences to be detected by a multiplex target detection with a highest target coverage by using a limited number of oligonucleotides in a pool of oligonucleotides, comprising (a) a computer processor, and (b) a computer readable storage medium of the present method coupled to the computer processor.

In another aspect of this invention, there is provided a computer readable storage medium containing instructions to configure a processor to perform a method for determining a conserved region in a plurality of target nucleic acid sequences, the method comprising: (i) aligning the plurality of target nucleic acid sequences; (ii) preparing the pool of oligonucleotides to be hybridized with the plurality of target nucleic acid sequences; (iii) selecting from the pool of oligonucleotides a least oligonucleotide combination with a target coverage of interest for the plurality of target nucleic acid sequences; wherein the selection of the least oligonucleotide combination is performed to achieve the following objective formula 1 together with satisfying the following constraint formulas 1 and 2, or the constraint formula 2:

$$\text{Min: } \sum_{p=1}^{a} x_p \quad \text{Objective formula 1}$$

wherein Min: represents minimization, $x_p$ is a binary variable consisting of a non-selection value ($x_{non\text{-}sel}$) and a selection value ($x_{sel}$) for whether or not an oligonucleotide p is selected, and p is a serial number of the oligonucleotide p ranging from 1 to a;

$$\sum_{s=1}^{b} c_s \geq m \times S \quad \text{Constraint formula 1}$$

wherein $c_s$ is a binary variable consisting of a non-coverage value ($c_{non\text{-}cov}$) and a coverage value ($c_{cov}$) for whether or not a target nucleic acid sequence s is covered, m is a target coverage of interest with a value of $0<m<1$, S is the total number of the plurality of target nucleic acid sequences, and s is a serial number of a target nucleic acid sequence s ranging from 1 to b;

$$\sum_{p=1}^{a} y_{s,p} x_p \geq c_s \text{ for all } s \quad \text{Constraint formula 2}$$

wherein $y_{s,p}$ is a binary constant consisting of a non-coverage value ($y_{non\text{-}cov}$) and a coverage value ($y_{cov}$) representing whether or not a target nucleic acid sequence s is covered by an oligonucleotide p; $x_p$ is a binary variable for whether or not an oligonucleotide p is selected; $c_s$ is a binary variable for whether or not a target nucleic acid sequence s is covered in which $c_s$ is a coverage value ($c_{cov}$) when the target coverage of interest is 100% and $c_s$ is a non-coverage value ($c_{non\text{-}cov}$) and a coverage value ($c_{cov}$) when the target coverage of interest is less than 100%; and for all s represents application to all of target nucleic acid sequences s; and (iv) determining as the conserved region a region of the plurality of target nucleic acid sequences covered by the least oligonucleotide combination.

In still another aspect of this invention, there is provided a computer program to be stored on a computer readable storage medium, to configure a processor to perform a method for determining a conserved region in a plurality of target nucleic acid sequences, and the method is the same as the method described in the computer readable storage medium described above.

In still another aspect of this invention, there is provided a device for determining a conserved region in a plurality of target nucleic acid sequences, comprising (a) a computer processor, and (b) a computer readable storage medium of the present method coupled to the computer processor.

In another aspect of this invention, there is provided a computer readable storage medium containing instructions to configure a processor to perform a method for determining a conserved region in a plurality of target nucleic acid sequences, the method comprising: (i) aligning the plurality of target nucleic acid sequences; (ii) preparing the pool of oligonucleotides to be hybridized with the plurality of target nucleic acid sequences; (iii) selecting from the plurality of target nucleic acid sequences target nucleic acid sequences to be detected with a highest target coverage by using a limited number of oligonucleotides; wherein the selection of the target nucleic acid sequences to be detected is performed to achieve the following objective formula 2 together with satisfying the following constraint formulas 3 and 2:

$$\text{Max: } \sum_{s=1}^{b} c_s \qquad \text{Objective formula 2}$$

wherein Max: represents maximization, $c_s$ is a binary variable consisting of a non-coverage value ($c_{non\text{-}cov}$) and a coverage value ($c_{cov}$) for whether or not a target nucleic acid sequence s is covered, s is a serial number of a target nucleic acid sequence s ranging from 1 to b;

$$\sum_{p=1}^{a} x_p \leq X_{Lim} \qquad \text{Constraint formula 3}$$

wherein $x_p$ is a binary variable consisting of a non-selection value ($x_{non\text{-}cov}$) and a selection value ($x_{sel}$) for whether or not an oligonucleotide p is selected, p is a serial number of the oligonucleotide p ranging from 1 to a, and $X_{Lim}$ is a limited number of the oligonucleotide;

$$\sum_{p=1}^{a} y_{s,p} x_p \geq c_s \text{ for all } s \qquad \text{Constraint formula 2}$$

wherein $y_{s,p}$ is a binary constant consisting of a non-coverage value ($y_{non\text{-}cov}$) and a coverage value ($y_{cov}$) representing whether or not a target nucleic acid sequence s is covered by an oligonucleotide p; $x_p$ is a binary variable for whether or not an oligonucleotide p is selected; $c_s$ is a binary variable for whether or not a target nucleic acid sequence s is covered in which $c_s$ is a coverage value ($c_{cov}$) when the target coverage of interest is 100% and $c_s$ is a non-coverage value ($c_{non\text{-}cov}$) and a coverage value ($c_{cov}$) when the target coverage of interest is less than 100%; and for all s represents application to all of target nucleic acid sequences s; and (iv) determining as the conserved region a region of the target nucleic acid sequences to be detected with the highest target coverage by the limited number of oligonucleotides.

In still another aspect of this invention, there is provided a computer program to be stored on a computer readable storage medium, to configure a processor to perform a method for determining a conserved region in a plurality of target nucleic acid sequences, and the method is the same as the method described in the computer readable storage medium described above.

In still another aspect of this invention, there is provided a device for determining a conserved region in a plurality of target nucleic acid sequences, comprising (a) a computer processor, and (b) a computer readable storage medium of the present method coupled to the computer processor.

Since the storage medium, the device and the computer program of the prevent invention are intended to perform the present methods described hereinabove in a computer, the common descriptions between them are omitted in order to avoid undue redundancy leading to the complexity of this specification.

The program instructions are operative, when performed by the processor, to cause the processor to perform the present method described above. The program instructions for performing the present method described above may comprise the following instructions: (i) an instruction to select from a pool of oligonucleotides a least oligonucleotide combination that achieves the objective formula 1 together with satisfying the constraint formulas 1 and 2, or the constraint formula 2, or (ii) an instruction to select target nucleic acid sequences to be detected that achieves the objective formula 2 together with satisfying the constraint formulas 3 and 2. In addition, the program instructions may include at least one of the following instructions: (iii) an instruction to collect a plurality of target nucleic add sequences from a database for nucleic acid sequences, (iv) an instruction to prepare a pool of oligonucleotides that are hybridized with a plurality of target nucleic acid sequences, (v) an instruction to align a plurality of target nucleic acid sequences.

The storage medium and the device of the present invention may include a database of nucleic acid sequences and/or a database of a pool of oligonucleotides hybridized with a plurality of target nucleic acid sequences.

The present method is implemented in a processor, such as a processor in a stand-alone computer or a network attached computer.

The types of the computer readable storage medium include various storage medium such as CD-R, CD-ROM, DVD, flash memory, floppy disk, hard drive, portable HDD, USB, magnetic tape, MINIDISC, nonvolatile memory card, EEPROM, optical disk, optical storage medium, RAM, ROM, system memory and web server.

The oligonucleotides, target nucleic acid sequences and/or conserved region selected by the present invention may be provided in a variety of ways. For example, the selected oligonucleotides, target nucleic acid sequences and/or conserved region may be provided to a separate system such as a desktop computer system via a network connection (e.g., LAN, VPN, intranet and Internet) or direct connection (e.g., USB or other direct wired or wireless connection), or provided on a portable medium such as a CD, DVD, floppy disk and portable HDD. Similarly, the selected oligonucleotides, target nucleic acid sequences and/or conserved region may be provided to a server system via a network connection (e.g., LAN, VPN, Internet, intranet and wireless communication network) to a client such as a notebook or a desktop computer system.

The instructions to configure the processor to perform the present invention may be included in a logic system. The instructions may be downloaded and stored in a memory module (e.g., hard drive or other memory such as a local or attached RAM or ROM), although the instructions can be provided on any software storage medium such as a portable HDD, USB, floppy disk, CD and DVD. A computer code for implementing the present invention may be implemented in a variety of coding languages such as C, C++, Java, Visual Basic, VBScript, JavaScript, Peri and XML. In addition, a variety of languages and protocols may be used in external and internal storage and transmission of data and commands according to the present invention.

The computer processor may be prepared in such a manner that a single processor can do several performances. Alternatively, the processor unit may be prepared in such a manner that several processors do the several performances, respectively.

The features and advantages of this invention are summarized as follows:

(a) When several oligonucleotides are used to detect a plurality of nucleic acid sequences of a target nucleic acid molecule exhibiting genetic diversity, the conventional methods for determining an optimal oligonucleotide combination are likely to be empirical and manual, which are a time-consuming and labor-consuming process with poor accuracy.

Unlike the conventional methods described above, the present invention may present an optimal combination of oligonucleotides in a logical and automatic manner, thereby solving problems of the conventional methods. The method of the present invention is much more rapid and accurate than any conventional method.

(b) The optimization logic of the present invention is versatile in application to detection of target nucleic acid molecules, which is a prominent feature over any publicly known methods. The optimization logic of the present invention may be used to (i) preparing an oligonucleotide combination used to detect a plurality of target nucleic acid sequences with a target coverage of interest, (ii) selecting target nucleic acid sequences to be detected by a multiplex target detection with a highest target coverage by using a limited number of oligonucleotides, and (iii) determining a conserved region in a plurality of target nucleic acid sequences.

(c) The present invention becomes more highlighted for selecting and preparing an oligonucleotide combination from a massive oligonucleotide pool to detect a plurality of pathogens with genetic diversity such as virus or to screen bacteria genus (e.g., *Campylobacter, Salmonella, Shigella, Vibrio* and *Aeromonas*).

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1: Alignment of Target Nucleic Acid Sequences

Thirty-nine (39) complete genomic sequences of *Mycobacterium tuberculosis* (SEQ ID Nos: 1 to 39) as a plurality of target nucleic acid sequences collected from National Center for Biotechnology Information (NCBI) were aligned and serial numbers were assigned to the collected genomic nucleic acid sequences of *Mycobacterium tuberculosis*. The accession numbers of SEQ ID Nos:1 to 39 in NCBI GenBank are CP008983, AP017901, CP016888, CP008967, CP005082, CP004886, CP003234, CP018305, CP010339, CP008978, CP007809, CP010895, CP010330, CP008965, CP001664, CP010336, CP010334, F0203509, CP008975, CP009427, CP010333, CP008973, CP007803, F0203510, CP014617, CP008976, CP002885, AP012340, CP008974, CP018301, CP010338, CP003248, HE572590, AP014573, CP007299, CP007027, CP009426, AL123456 and CP009480, respectively.

Example 2: Probe Library for Target Nucleic Acid Sequences

Probes in 24-28 bp long being hybridizable with each of the plurality of target nucleic acid sequences of *Mycobacterium tuberculosis* were designed and a probe library comprising the designed probes was constructed. Serial numbers were assigned to the probes included in the probe library. In the probe library, probes differ in probing regions; where probing regions are the same, they differ in probe sequence and/or length.

Example 3: Matrix for Probes Covering Target Nucleic Acid Sequences

As shown in FIG. 2, a coverage value and a non-coverage value indicating whether the target nucleic acid sequences are covered by probes or not were represented by a binary matrix. In FIG. 2, when the probe covers the target nucleic acid sequence, the coverage value is indicated as 1, and when the probe does not cover the target nucleic acid sequence, the non-coverage value is indicated as 0. In FIG. 2, the coverage refers to 100% match of a probe to a target nucleic acid sequence and the non-coverage refers to less than 100% match of a probe to a target nucleic acid sequence.

For example, in order to describe probes covering target nucleic acid sequences by a matrix, the coverage and the non-coverage of probes (26 bp in length) of Nos. 14499, 17228 and 18744 to target nucleic acid sequences of Nos. 49 to 77 were represented as a matrix by applying a binary constant (0 or 1) ($Y=\{y_{s,p}$ for all probes (p) and sequences (s), $y_{s,p}\in(0, 1)\}$) (Table 1).

TABLE 1

| | Probe No (p) | | |
|---|---|---|---|
| Sequence No (s) | 14499 | 17228 | 18744 |
| 49 | 0 | 0 | 0 |
| 50 | 0 | 0 | 0 |
| 51 | 1 | 0 | 0 |
| 52 | 0 | 0 | 0 |
| 53 | 0 | 0 | 0 |
| 54 | 0 | 0 | 0 |
| 55 | 0 | 0 | 0 |
| 56 | 0 | 0 | 0 |
| 57 | 0 | 0 | 0 |
| 58 | 0 | 0 | 0 |
| 59 | 0 | 0 | 0 |
| 60 | 0 | 0 | 0 |
| 61 | 0 | 0 | 0 |
| 62 | 0 | 0 | 0 |
| 63 | 0 | 0 | 0 |
| 64 | 0 | 1 | 0 |
| 65 | 0 | 1 | 0 |
| 66 | 0 | 0 | 0 |
| 67 | 0 | 0 | 0 |
| 68 | 0 | 0 | 0 |
| 69 | 0 | 0 | 0 |
| 70 | 0 | 0 | 0 |
| 71 | 0 | 0 | 0 |
| 72 | 0 | 0 | 1 |
| 73 | 0 | 0 | 0 |
| 74 | 0 | 0 | 0 |
| 75 | 0 | 0 | 0 |
| 76 | 0 | 0 | 1 |
| 77 | 0 | 0 | 0 |

$y_{s,p}$ is a binary constant (0 or 1) indicating whether a probe p covers a sequence s, s is a subscript indicating a sequence ID (serial number) (s=1, 2, . . . , b), b represents ID of the last sequence, p represents a subscript indicating probe ID (serial number) (p=1, 2, . . . , a), and a represents ID of the last probe. For example, $y_{s,p}=0$ means that a probe p does not cover a sequence s, and $y_{s,p}=1$ means that a probe p covers a sequence s. The results of Table 1 are briefly summarized as shown in Table 2:

TABLE 2

| Probe ID | Sequence ID | Sequence ID | $y_{s,p}$ |
|---|---|---|---|
| 14499 | 51 | — | $y_{51,14499}=1$, $y_{s,14499}=0$ $(s \neq 51)$ |
| 17228 | 64 | 65 | $y_{64,17228}=1$, $y_{65,17228}=1$, $y_{s,17228}=0$ $(s \neq 64, 65)$ |
| 18744 | 72 | 76 | $y_{72,18744}=1$, $y_{76,18744}=1$, $y_{s,18744}=0$ $(s \neq 72, 76)$ |

Example 4: Determination of Least Probe Combination Covering All Target Nucleic Acid Sequences Using Linear Programming Algorithm When several probes were used to detect the plurality of target nucleic acid sequences, a linear programming algorithm was applied to provide optimization logic for selection of an optimal probe combination.

An example of probes covering target nucleic acid sequences are schematically shown in FIG. 3. For example, the probe 1 covers the sequences 7 and 9, the probe 2 covers the sequences 5, 7, 8, 9 and 10 at different positions from the probe 1, and the probe 3 covers the sequences 7 and 8. The coverage values and non-coverage values of the sequences 1 to 10 by the probes 1 to 10 were represented by a 10×10 binary matrix ($Y=\{y_{s,p}, y_{s,p}\in(0, 1)\}$), as summarized in FIG. 4. When a probe covers a sequence, $y_{s,p}=1$ was assigned, and when a probe does not cover, $y_{s,p}=0$ was assigned. For example, because the sequence 1 is covered by the probes 6, 7 and 9 but not covered by the probes 1 to 5 and 10, it was expressed as $y_{1,6}=y_{1,7}=y_{1,9}=1$ and $y_{1,1}=y_{1,2}=y_{1,3}=y_{1,4}=y_{1,5}=y_{1,10}=0$.

A binary variable $x_p$ indicating whether a probe p is selected was set as a decision variable: $x_p=1$ when a probe p is selected, and $x_p=0$ when a probe p is not selected.

Therefore, $Z=x_1+Fx_2+x_3+x_4+x_5+x_6+x_7+x_8+x_9+x_{10}$ is an objective function representing the number of selected probes which is intended to minimize.

In addition, a constraint to cover all target nucleic acid sequences has to be satisfied. For example, the constraint formula showing that the sequence 1 is covered by any one of the probes 1 to 10 can be expressed as $y_{1,1}x_1+y_{1,2}x_2+y_{1,3}x_2+y_{1,4}x_4+y_{1,5}x_5+y_{1,6}x_6+y_{1,7}x_7+y_{1,8}x_8+y_{1,9}x_9+y_{1,10}x_{10}\geq 1$, Here, $y_{1,p}x_p$ is a binary variable indicating whether or not the sequence 1 is covered by probe p and whether or not probe p is selected. In the case of $y_{1,1}x_1=1$, it indicates that the sequence 1 is covered by the probe 1 and the probe 1 is selected. In the case of $y_{1,1}x_1=0$, it indicates that the sequence 1 is not covered by the probe 1, or the probe 1 is not selected even if the sequence 1 is covered by the probe 1.

Thus, the linear programming problem with the constraint formula in which selected probes cover all of the sequences 1 to 10 may be summarized as Table 3 below. Program MATLAB R2015b was used to obtain an optimal solution of the linear programming problem.

TABLE 3 minimize $Z = x_1 + x_2 + x_3 + x_4 + x_5 + x_6 + x_7 + x_8 + x_9 + x_{10}$ subject to $$x_6 + x_7 + x_9 \geq 1$$
$$x_4 \geq 1$$
$$x_6 + x_8 \geq 1$$
$$x_8 + x_{10} \geq 1$$
$$x_2 \geq 1$$
$$x_7 \geq 1$$
$$x_1 + x_2 + x_3 + x_4 + x_5 + x_6 + x_8 + x_9 + x_{10} \geq 1$$
$$x_2 + x_3 + x_7 \geq 1$$
$$x_1 + x_2 + x_5 + x_6 \geq 1$$
$$x_2 + x_7 \geq 1$$

and $x_p \in \{0, 1\}$ f or p = 1, 2, 3, 4, 5, 6, 7, 8, 9, 10

In Table 3, the above-described constraint formula $y_{1,1}x_1+y_{1,2}x_2+y_{1,3}x_3+y_{1,4}x_4+y_{1,5}x_5+y_{1,6}x_6+y_{1,7}x_7+y_{1,8}x_8+y_9x_9+y_{1,10}x_{10}\geq 1$ is formulated for all the 10 target nucleic acid sequences.

As a result, the optimal solution of the problem obtained using MATLAB R2015b was calculated as $x_1=0$, $x_2=1$, $x_3=0$, $x_4=1$, $x_5=0$, $x_6=0$, $x_7=1$, $x_8=1$, $x_9=0$, $x_{10}=0$. That is, in order to cover all of the sequences 1 to 10, at least four probes are required and the probe combination set is the probe 2, the probe 4, the probe 7 and the probe 8.

Example 5: Determination of Target Nucleic Acid Sequences Covered with Highest Target Coverage Using a Limited Number of Probes by Linear Programming Algorithm Following examples of FIG. 3, $c_s=x_{p+s}$ (p=a) was introduced as a new decision variable in addition to the decision variable $x_p$ of Example 4 for maximizing target nucleic acid sequences covered by a limited number of probes, a constraint formula and an objective function were defined. The decision variable $c_s$ is a binary variable indicating whether a sequence s is covered, and $c_s$ may be represented by $x_{p+s}$ in which p represents ID of the last probe (i.e., the serial number a of the last probe). For example, $c_4=x_{10+4}=x_{14}=0$ when not covering the sequence 4, and $c_4=x_{10+4}=x_{14}=1$ when the sequence 4 is intended to be covered. Since the sequences to be covered as many as possible have to be determined, $Z=c_1+c_2+c_3+c_4+c_3+c_6+c_7+c_8+c_9+c_{10}=x_{11}+x_{12}+x_{13}+x_{14}+x_{15}+x_{16}+x_{17}+x_{19}+x_{20}$ is an ojective function which is intended to maximize. Assuming that the number of probes is limited to two, the constraint formula for this becomes $x_1+x_2+x_3+x_4+x_5+x_6+x_7+x_8+x_9+x_{10}\leq 2$ (constraint formula 1), and since the selected probe covers only the sequences intended to be covered (i.e., it does not cover all sequences), the constraint formula for this becomes $c_s=x_{10+s}\leq y_{s,1}x_1+y_{s,2}x_2+y_{s,3}x_3+y_{s,4}x_4+y_{s,5}x_5+y_{s,6}x_6+y_{s,7}x_7+y_{s,8}x_8+y_{s,9}x_9+y_{s,10}x_{10}$ constraint formula 2; s represents ID of target nucleic acid sequences, i.e., the serial number of target nucleic acid sequences).

In the constraint formula 2, in order to become $c_s=x_{10+s}=1$, the value of the right side has to be unconditionally 1 or more. As described in Example 4, the right side of the constraint formula 2 indicates which probe among the probes 1 to 10 cover the sequence s, and therefore it has a value of 1 or more whenever it is covered by any probe, and 0 if not covered. In order to cover the sequence s in the constraint formula 2, it has to be covered by at least one of the probes 1 to 10.

The linear programming problem that maximizes the objective function while satisfying the constraint formulas 1 and 2 was summarized in the following Table 4 and the optimal solution of the problem was obtained using the program MATLAB R2015b.

TABLE 4

| | | |
|---|---|---|
| Maximize Z | $= C_1 + C_2 + C_3 + C_4 + C_5 + C_6 + C_7 + C_8 + C_9 + C_{20}$ | |
| | $= x_{11} + x_{12} + x_{13} + x_{14} + x_{15} + x_{16} + x_{17} + x_{18} + x_{19} + x_{20}$ | |
| subject to | | |
| | $x_6 + x_7 + x_9 - x_{11}$ | $\geq 0$ |
| | $x_4 - x_{12}$ | $\geq 0$ |
| | $x_6 + x_8 - x_{13}$ | $\geq 0$ |
| | $x_8 + x_{10} - x_{14}$ | $\geq 0$ |
| | $x_2 - x_{15}$ | $\geq 0$ |
| | $x_7 - x_{16}$ | $\geq 0$ |
| | $x_1 + x_2 + x_5 + x_6 + x_8 - x_{17}$ | $\geq 0$ |
| | $x_2 + x_3 + x_5 + x_7 - x_{18}$ | $\geq 0$ |
| | $x_1 + x_2 + x_5 + x_6 - x_{19}$ | $\geq 0$ |
| | $x_2 + x_5 + x_7 - x_{20}$ | $\geq 0$ |
| | $x_1 + x_2 + x_3 + x_4 + x_5 + x_6 + x_7 + x_8 + x_9 + x_{10}$ | $\leq 2$ |
| and | | |
| | $x_p \in \{0,1\}$ f or p = 1, 2, 3, 4, 5, 6, 7, 8, 9, 10, $C_s = x_{10+s} \in \{0,1\}$ f or s = 1,2,3,4,5,6,7,8,9,10 | |

In Table 4, the above-described constraint formula 2 $c_s=x_{10+s}\leq y_{s,1}x_1+y_{s,2}x_2+y_{s,3}x_3+y_{s,4}x_4+y_{s,5}x_5+y_{s,6}x_6+y_{s,7}x_7+y_{s,8}x_8+y_{s,9}x_9+y_{s,10}x_{10}$ is formulated for all the 10 target nucleic acid sequences.

As a result, the optimal solution of the above problem obtained using MATLAB R2015b was calculated as $x_1=0$, $x_2=0$, $x_3=0$, $x_4=0$, $x_5=0$, $x_6=0$, $x_7=1$, $x_8=1$, $x_9=0$, $x_{10}=0$, $c_1=x_{11}=1$, $c_2=x_{12}=0$, $c_3=x_{13}=1$, $c_4=x_{14}=1$, $c_5=x_{15}=0$, $c_6=x_{16}=1$, $c_y=x_{17}=1$, $c_8=x_{18}=1$, $c_9=x_{19}=0$, $c_{10}=x_{20}=1$. That is, the maximum sequences to be covered using the probes 7 and 8 are 7 sequences (sequences 1, 3, 4, 6-8 and 10) out of 10 sequences.

Example 6: Determine of Least Probe Combination with Coverage Above a Certain Value Using Linear Programming Algorithm Following examples of FIG. 3, $x_p$ and $c_s=x_{p+s}$ were determined as decision variables, and a constraint formula and an objective function were defined in order to determine a least probe combination satisfying a coverage of 90% or more. The number of probes has to be minimized and therefore the objective function becomes $Z=x_1+x_2+x_3+x_4+x_5+x_6+x_7+x_8+x_9+x_{10}$, and the coverage of at least 90% has to be satisfied and therefore the constraint formula 1 was expressed as $c_1+c_2+c_3+c_4+c_5+c_6+c_7+c_8+c_9+c_{10}=x_{11}+x_{12}+x_{13}+x_{14}+x_{15}+x_{16}+x_{17}+x_{19}+x_{20}\geq 0.90\times 10$ (the lowest coverage×the total number of the sequences). Furthermore, as the selected probe covers only the sequences intended to be covered (i.e., it does not cover all sequences), the constraint formula 2 for this was expressed as $c_s=x_{10+s}\leq y_{s,1}x_1+y_{s,2}x_2+y_{s,3}x_3+y_{s,4}x_4+y_{s,5}x_5+y_{s,6}x_6+y_{s,7}x_7+y_{s,8}x_8+y_{s,9}x_9+y_{s,10}x_{10}$ (In the constraint formula 2, s represents ID of target nucleic acid sequences, i.e., the serial number of target nucleic acid sequences).

The linear programming problem minimizing the objective function while satisfying the constraint formulas 1 and 2 was summarized in Table 5 and the optimal solution of the problem was obtained using the program MATLAB R2015b.

TABLE 5

| | | |
|---|---|---|
| | 'minimize Z' $= x_1 + x_2 + x_3 + x_4 + x_5 + x_6 + x_7 + x_8 + x_9 + x_{10}$ | |
| subject to | | |
| | $x_6 + x_7 + x_9 - x_{11}$ | $\geq 0$ |
| | $x_4 - x_{12}$ | $\geq 0$ |
| | $x_6 + x_8 - x_{13}$ | $\geq 0$ |
| | $x_8 + x_{10} - x_{14}$ | $\geq 0$ |
| | $x_2 - x_{15}$ | $\geq 0$ |
| | $x_7 - x_{16}$ | $\geq 0$ |
| | $x_1 + x_2 + x_5 + x_6 + x_8 - x_{17}$ | $\geq 0$ |
| | $x_2 + x_3 + x_5 + x_7 - x_{18}$ | $\geq 0$ |
| | $x_1 + x_2 + x_5 + x_6 - x_{19}$ | $\geq 0$ |
| | $x_2 + x_5 + x_7 - x_{20}$ | $\geq 0$ |
| | $x_{11} + x_{12} + x_{13} + x_{14} + x_{15} + x_{16} + x_{17} + x_{18} + x_{19} + x_{20}$ | $\geq 9$ |
| and | | |
| | $x_p \in \{0,1\}$ f or p = 1, 2, 3, 4, 5, 6, 7, 8, 9, 10, $C_s = x_{10+s} \in \{0,1\}$ f or s = 1,2,3,4,5,6,7,8,9,10 | |

In Table 5, the above-described constraint formula 2 $c_s=X_{10+s}\leq y_{s,1}x_1+y_{s,2}x_2+y_{s,3}x_3+y_{s,4}x_4+y_{s,5}x_5+y_{s,6}x_6+y_{s,7}x_7+y_{s,8}x_8+y_{s,9}x_9+y_{s,10}x_{10}$ is formulated for all the 10 target nucleic acid sequences.

As a result, the optimal solution of the problem obtained using MATLAB R2015b was calculated as $x_1=0$, $x_2=1$, $x_3=0$, $x_4=0$, $x_5=0$, $x_6=0$, $x_7=1$, $x_8=1$, $x_9=0$, $x_{10}=0$, $c_1=x_{11}=1$, $c_2=x_{12}=0$, $c_3=x_{13}=1$, $c_4=x_{14}=1$, $c_5=x_{13}=1$, $c_6=x_{16}=1$, $c_7=x_{17}=1$, $c_8=x_{18}=1$, $c_9=x_{19}=1$, $c_{10}=x_{20}=1$. That is, the least probe combination satisfying the coverage of 90% or more was determined as the probe 2, the probe 7 and the probe 8. Furthermore, the sequences to be covered by the least probe combination were determined as the sequence 1 and the sequences 3 to 10.

Having described a preferred embodiment of the present invention, it is to be understood that variants and modifications thereof falling within the spirit of the invention may become apparent to those skilled in this art, and the scope of this invention is to be determined by appended claims and their equivalents.

This application contains references to amino acid sequences and/or nucleic acid sequences which have been submitted herewith as the sequence listing text file. The aforementioned sequence listing is hereby incorporated by reference in its entirety pursuant to 37 C.F.R. § 1.52(e).

What is claimed is:

1. A computer-implemented method for preparing a combination of oligonucleotides used to detect a plurality of target nucleic acid sequences with a target coverage of interest from a pool of oligonucleotides, comprising:

(a) preparing the plurality of target nucleic acid sequences;

(b) preparing the pool of oligonucleotides to be hybridized with the plurality of target nucleic acid sequences;

(c) selecting from the pool of oligonucleotides a combination of a minimum number of oligonucleotides with the target coverage of interest for the plurality of target nucleic acid sequences; wherein the selection of the combination of the minimum number of oligonucleotides is performed to achieve the following objective formula 1 together with satisfying the following constraint formulas 1 and 2, or the constraint formula 2; and, (d) preparing the combination of the minimum number of oligonucleotides selected in step (c); and $$\text{Min: } \sum_{p=1}^{a} x_p \qquad \text{Objective formula 1}$$

wherein Min: represents minimization, $x_p$ is a binary variable consisting of a non-selection value ($X_{non\text{-}sel}$) and a selection value ($x_{sel}$) for whether or not an oligonucleotide p is selected, and p is a serial number of the oligonucleotide p ranging from 1 to a;

$$\sum_{s=1}^{b} c_s \geq m \times S \qquad \text{Constraint formula 1}$$

wherein $c_s$ is a binary variable consisting of a non-coverage value ($c_{non\text{-}cov}$) and a coverage value ($c_{cov}$) for whether or not a target nucleic acid sequence s is covered, m is a target coverage of interest with a value of $0<m<1$, S is the total number of the plurality of target nucleic acid sequences, and s is a serial number of a target nucleic acid sequence s ranging from 1 to b;

$$\sum_{p=1}^{a} y_{s,p} x_p \geq c_s \text{ for all } s \qquad \text{Constraint formula 2}$$

wherein $y_{s,p}$ is a binary constant consisting of a non-coverage value ($y_{non\text{-}cov}$) and a coverage value ($y_{cov}$) representing whether or not a target nucleic acid sequence s is covered by an oligonucleotide p; $x_p$ is a binary variable for whether or not an oligonucleotide p is selected; $c_s$ is a binary variable for whether or not a target nucleic acid sequence s is covered in which $c_s$ is a coverage value ($c_{cov}$) when the target coverage of interest is 100% and $c_s$ is a non-coverage value ($c_{non\text{-}cov}$) and a coverage value ($c_{cov}$) when the target coverage of interest is less than 100%; and for all s represents application to all of target nucleic acid sequences s.

2. The method according to claim 1, wherein the method is performed to achieve the objective formula 1 together with satisfying the constraint formulas 1 and 2 when the target coverage of interest is less than 100%, whereby the combination of the minimum number of oligonucleotides is selected and target nucleic acid sequences covered by the selected combination of the minimum number of oligonucleotides are selected among the plurality of target nucleic acid sequences.

3. The method according to claim 1, wherein the method is performed to achieve the objective formula 1 together with satisfying the constraint formula 2 when the target coverage of interest is 100%.

4. The method according to claim 1, wherein the binary variable $c_s$ of the constraint formula 2 is $x_{a+s}$ in which a is the last serial number of an oligonucleotide p and s is a serial number of a target nucleic acid sequence s ranging from 1 to b.

5. The method according to claim 1, wherein the non-selection value ($x_{non\text{-}sel}$) and the selection value ($x_{sel}$) of the $x_p$ are 0 and 1, respectively.

6. The method according to claim 1, wherein the non-coverage value ($c_{non\text{-}cov}$) and the coverage value ($c_{cov}$) of the $c_s$ are 0 and 1, respectively.

7. The method according to claim 1, wherein the non-coverage value ($y_{non\text{-}cov}$) and the coverage value ($y_{cov}$) of the $y_{s,p}$ are 0 and 1, respectively.

8. The method according to claim 1, wherein the plurality of target nucleic acid sequences are a plurality of nucleic acid sequences having sequence similarity for one target nucleic acid molecule exhibiting genetic diversity.

9. The method according to claim 1, wherein the plurality of target nucleic acid sequences are a plurality of nucleic acid sequences from a plurality of organisms corresponding to homologues having the same function, the same structure, or the same gene name.

10. The method according to claim 1, wherein the pool of oligonucleotides comprises oligonucleotides that are hybridized with at least one sequence of the plurality of target nucleic acid sequences, and the oligonucleotides in the pool of oligonucleotides differ in a hybridization region and/or length from each other.

11. A non-transitory computer readable storage medium containing instructions to configure a processor to perform a method for preparing a combination of oligonucleotides used to detect a plurality of target nucleic acid sequences with a target coverage of interest from a pool of oligonucleotides, the method comprising:

selecting from the pool of oligonucleotides a combination of the minimum number of oligonucleotides with the target coverage of interest for the plurality of target nucleic acid sequences; wherein the selection of the combination of the minimum number of oligonucleotides is performed to achieve the following objective formula 1 together with satisfying the following constraint formulas 1 and 2, or the constraint formula 2:

$$\text{Min: } \sum_{p=1}^{a} x_p \qquad \text{Objective formula 1}$$

wherein Min: represents minimization, $x_p$ is a binary variable consisting of a non-selection value ($x_{non-sel}$) and a selection value ($x_{sel}$) for whether or not an oligonucleotide p is selected, and p is a serial number of the oligonucleotide p ranging from 1 to a;

$$\sum_{s=1}^{b} c_s \geq m \times S \qquad \text{Constraint formula 1}$$

wherein $c_s$ is a binary variable consisting of a non-coverage value ($c_{non-cov}$) and a coverage value ($c_{cov}$) for whether or not a target nucleic acid sequence s is covered, m is a target coverage of interest with a value of 0<m<1, S is the total number of the plurality of target nucleic acid sequences, and s is a serial number of a target nucleic acid sequence s ranging from 1 to b;

$$\sum_{p=1}^{a} y_{s,p} x_p \geq c_s \text{ for all } s \qquad \text{Constraint formula 2}$$

wherein $y_{s,p}$ is a binary constant consisting of a non-coverage value ($y_{non-cov}$) and a coverage value ($y_{cov}$) representing whether or not a target nucleic acid sequence s is covered by an oligonucleotide p; $x_p$ is a binary variable for whether or not an oligonucleotide p is selected; $c_s$ is a binary variable for whether or not a target nucleic acid sequence s is covered in which $c_s$ is a coverage value ($c_{cov}$) when the target coverage of interest is 100% and $c_s$ is a non-coverage value ($c_{non-cov}$) and a coverage value ($c_{cov}$) when the target coverage of interest is less than 100%; and for all s represents application to all of target nucleic acid sequences s.

* * * * *

```
                                SEQUENCE LISTING


<160> NUMBER OF SEQ ID NOS: 39

<210> SEQ ID NO 1
<211> LENGTH: 79
<212> TYPE: DNA
<213> ORGANISM: Mycobacterium tuberculosis

<400> SEQUENCE: 1

accggatatc ttagctggtc aatagccatt tttcagcaat ttctcagtaa cgctacgggg      60

cgcgccgtgc cgtagtagc                                                   79


<210> SEQ ID NO 2
<211> LENGTH: 79
<212> TYPE: DNA
<213> ORGANISM: Mycobacterium tuberculosis

<400> SEQUENCE: 2

accggatatc ttagctggtc aatagccatt tttcagcaat ttctcagtaa cgctacgggg      60

cgcgccgtgc cgtagtagc                                                   79


<210> SEQ ID NO 3
<211> LENGTH: 79
<212> TYPE: DNA
<213> ORGANISM: Mycobacterium tuberculosis

<400> SEQUENCE: 3

accggatatc ttagctggtc aatagccatt tttcagcaat ttctcagtaa cgctacgggg      60

cgcgccgtgc cgtagtagc                                                   79


<210> SEQ ID NO 4
<211> LENGTH: 79
<212> TYPE: DNA
<213> ORGANISM: Mycobacterium tuberculosis

<400> SEQUENCE: 4

accggatatc ttagctggtc aatagccatt tttcagcaat ttctcagtaa cgctacgggg      60

cgcgccgtgc cgtagtagc                                                   79


<210> SEQ ID NO 5
<211> LENGTH: 79
<212> TYPE: DNA
<213> ORGANISM: Mycobacterium tuberculosis

<400> SEQUENCE: 5

accggatatc ttagctggtc aatagccatt tttcagcaat ttctcagtaa cgctacgggg      60

cgcgccgtgc cgtagtagc                                                   79


<210> SEQ ID NO 6
<211> LENGTH: 79
<212> TYPE: DNA
<213> ORGANISM: Mycobacterium tuberculosis

<400> SEQUENCE: 6

accggrtatc ttagctggtc aatagccatt tttcagcaat ttctcagtaa cgctacgggg      60

cgcgccgtgc cgtagtagc                                                   79
```

<210> SEQ ID NO 7
<211> LENGTH: 79
<212> TYPE: DNA
<213> ORGANISM: Mycobacterium tuberculosis

<400> SEQUENCE: 7
accggatatc ttagctggtc aatagccatt tttcagcaat ttctcagtaa cgctacgggg 60
cgcgccgtgc cgtagtagc 79

<210> SEQ ID NO 8
<211> LENGTH: 79
<212> TYPE: DNA
<213> ORGANISM: Mycobacterium tuberculosis

<400> SEQUENCE: 8
accggatatc ttagctggtc aatagccatt tttcagcaat ttctcagtaa cgctacgggg 60
cgcgccgtgc cgtagtagc 79

<210> SEQ ID NO 9
<211> LENGTH: 79
<212> TYPE: DNA
<213> ORGANISM: Mycobacterium tuberculosis

<400> SEQUENCE: 9
accggatatc ttagctggtc aatagccatt tttcagcaat ttctcagtaa cgctacgggg 60
cgcgccgtgc cgtagtagc 79

<210> SEQ ID NO 10
<211> LENGTH: 79
<212> TYPE: DNA
<213> ORGANISM: Mycobacterium tuberculosis

<400> SEQUENCE: 10
accggatatc ttagctggtc aatagccatt tttcagcaat ttctcagtaa cgctacgggg 60
cgcgccgtgc cgtagtagc 79

<210> SEQ ID NO 11
<211> LENGTH: 79
<212> TYPE: DNA
<213> ORGANISM: Mycobacterium tuberculosis

<400> SEQUENCE: 11
accggatatc ttagctggtc aatagccatt tttcagcaat ttctcagtaa cgctacgggg 60
cgcgccgtgc cgtagtagc 79

<210> SEQ ID NO 12
<211> LENGTH: 79
<212> TYPE: DNA
<213> ORGANISM: Mycobacterium tuberculosis

<400> SEQUENCE: 12
accggatatc ttagctggtc aatagccatt tttcagcaat ttctcagtaa cgctacgggg 60
cgcgccgtgc cgtagtagc 79

<210> SEQ ID NO 13
<211> LENGTH: 79
<212> TYPE: DNA
<213> ORGANISM: Mycobacterium tuberculosis

<400> SEQUENCE: 13

-continued accggatatc ttagctggtc aatagccatt tttcagcaat ttctcagtaa cgctacgggg 60
cgcgccgtgc cgtagtagc 79

<210> SEQ ID NO 14
<211> LENGTH: 79
<212> TYPE: DNA
<213> ORGANISM: Mycobacterium tuberculosis

<400> SEQUENCE: 14
accggatatc ttagctggtc aatagccatt tttcagcaat ttctcagtaa cgctacgggg 60
cgcgccgtgc cgtagtagc 79

<210> SEQ ID NO 15
<211> LENGTH: 79
<212> TYPE: DNA
<213> ORGANISM: Mycobacterium tuberculosis

<400> SEQUENCE: 15
accggatatc ttagctggtc aatagccatt tttcagcaat ttctcagtaa cgctacgggg 60
cgcgtcgtgc cgtagtagc 79

<210> SEQ ID NO 16
<211> LENGTH: 79
<212> TYPE: DNA
<213> ORGANISM: Mycobacterium tuberculosis

<400> SEQUENCE: 16
accggatatc ttagctggtc aatagccatt tttcagcaat ttctcagtaa cgctacgggg 60
cgcgccgtgc cgtagtagc 79

<210> SEQ ID NO 17
<211> LENGTH: 79
<212> TYPE: DNA
<213> ORGANISM: Mycobacterium tuberculosis

<400> SEQUENCE: 17
accggatatc ttagctggtc aatagccatt tttcagcaat ttctcagtaa cgctacgggg 60
cgcgccgtgc cgtagtagc 79

<210> SEQ ID NO 18
<211> LENGTH: 79
<212> TYPE: DNA
<213> ORGANISM: Mycobacterium tuberculosis

<400> SEQUENCE: 18
gtcgctcatt ttagctggtc aaacactatt tttcagcaat atctcagtaa cgctacgggg 60
cgcgccgtgc cgtagtagc 79

<210> SEQ ID NO 19
<211> LENGTH: 79
<212> TYPE: DNA
<213> ORGANISM: Mycobacterium tuberculosis

<400> SEQUENCE: 19
accggatatc ttagctggtc aatagccatt tttcagcaat ttctcagtaa cgctacgggg 60
cgcgccgtgc cgtagtagc 79

<210> SEQ ID NO 20

-continued

<211> LENGTH: 79
<212> TYPE: DNA
<213> ORGANISM: Mycobacterium tuberculosis

<400> SEQUENCE: 20
accggatatc ttagctggtc aatagccatt tttcagcaat ttctcagtaa cgctacgggg 60
cgcgccgtgc cgtagtagc 79

<210> SEQ ID NO 21
<211> LENGTH: 79
<212> TYPE: DNA
<213> ORGANISM: Mycobacterium tuberculosis

<400> SEQUENCE: 21
accggatatc ttagctggtc aatagccatt tttcagcaat ttctcagtaa cgctacgggg 60
cgcgccgtgc cgtagtagc 79

<210> SEQ ID NO 22
<211> LENGTH: 79
<212> TYPE: DNA
<213> ORGANISM: Mycobacterium tuberculosis

<400> SEQUENCE: 22
accggatatc ttagctggtc aatagccatt tttcagcaat ttctcagtaa cgctacgggg 60
cgcgccgtgc cgtagtagc 79

<210> SEQ ID NO 23
<211> LENGTH: 79
<212> TYPE: DNA
<213> ORGANISM: Mycobacterium tuberculosis

<400> SEQUENCE: 23
accggatatc ttagctggtc aatagccatt tttcagcaat ttctcagtaa cgctacgggg 60
cgcgccgtgc cgtagtagc 79

<210> SEQ ID NO 24
<211> LENGTH: 79
<212> TYPE: DNA
<213> ORGANISM: Mycobacterium tuberculosis

<400> SEQUENCE: 24
accggatatc ttagctggtc aatagccatt tttcagcaat ttctcagtaa cgctacgggg 60
cacgccgtgc cgtagtagc 79

<210> SEQ ID NO 25
<211> LENGTH: 79
<212> TYPE: DNA
<213> ORGANISM: Mycobacterium tuberculosis

<400> SEQUENCE: 25
accggatatc ttagctggtc aatagccatt tttcagcaat ttctcagtaa cgctacgggg 60
cgcgccgtgc cgtagtagc 79

<210> SEQ ID NO 26
<211> LENGTH: 79
<212> TYPE: DNA
<213> ORGANISM: Mycobacterium tuberculosis

<400> SEQUENCE: 26
accggatatc ttagctggtc aatagccatt tttcagcaat ttctcagtaa cgctacgggg 60
cgcgccgtgc cgtagtagc 79

<210> SEQ ID NO 27
<211> LENGTH: 79
<212> TYPE: DNA
<213> ORGANISM: Mycobacterium tuberculosis

<400> SEQUENCE: 27
accggatatc ttagctggtc aatagccatt tttcagcaat ttctcagtaa cgctacgggg 60
cgcgccgtgc cgtagtagc 79

<210> SEQ ID NO 28
<211> LENGTH: 79
<212> TYPE: DNA
<213> ORGANISM: Mycobacterium tuberculosis

<400> SEQUENCE: 28
accggatatc ttagctggtc aatagccatt tttcagcaat ttctcagtaa cgctacgggg 60
cgcgtcgtgc cgtagtagc 79

<210> SEQ ID NO 29
<211> LENGTH: 79
<212> TYPE: DNA
<213> ORGANISM: Mycobacterium tuberculosis

<400> SEQUENCE: 29
accggatatc ttagctggtc aatagccatt tttcagcaat ttctcagtaa cgctacgggg 60
cgcgccgtgc cgtagtagc 79

<210> SEQ ID NO 30
<211> LENGTH: 79
<212> TYPE: DNA
<213> ORGANISM: Mycobacterium tuberculosis

<400> SEQUENCE: 30
accggatatc ttagctggtc aatagccatt tttcagcaat ttctcagtaa cgctacgggg 60
cgcgccgtgc cgtagtagc 79

<210> SEQ ID NO 31
<211> LENGTH: 79
<212> TYPE: DNA
<213> ORGANISM: Mycobacterium tuberculosis

<400> SEQUENCE: 31
accggatatc ttagctggtc aatagccatt tttcagcaat ttctcagtaa cgctacgggg 60
cgcgccgtgc cgtagtagc 79

<210> SEQ ID NO 32
<211> LENGTH: 79
<212> TYPE: DNA
<213> ORGANISM: Mycobacterium tuberculosis

<400> SEQUENCE: 32
accggatatc ttagctggtc aatagccatt tttcagcaat ttctcagtaa cgctacgggg 60
cgcgccgtgc cgtagtagc 79

<210> SEQ ID NO 33
<211> LENGTH: 79
<212> TYPE: DNA

<213> ORGANISM: Mycobacterium tuberculosis

<400> SEQUENCE: 33
accggatatc ttagctggtc aatagccatt tttcagcaat ttctcagtaa cgctacgggg 60
cgcgccgtgc cgtagtagc 79

<210> SEQ ID NO 34
<211> LENGTH: 79
<212> TYPE: DNA
<213> ORGANISM: Mycobacterium tuberculosis

<400> SEQUENCE: 34
accggatatc ttagctggtc aatagccatt tttcagcaat ttctcagtaa cgctacgggg 60
cgcgccgtgc cgtagtagc 79

<210> SEQ ID NO 35
<211> LENGTH: 79
<212> TYPE: DNA
<213> ORGANISM: Mycobacterium tuberculosis

<400> SEQUENCE: 35
accggatatc ttagctggtc aatagccatt tttcagcaat ttctcagtaa cgctacgggg 60
cgcgccgtgc cgtagtagc 79

<210> SEQ ID NO 36
<211> LENGTH: 79
<212> TYPE: DNA
<213> ORGANISM: Mycobacterium tuberculosis

<400> SEQUENCE: 36
accggatatc ttagctggtc aatagccatt tttcagcaat ttctcagtaa cgctacgggg 60
cgcgccgtgc cgtagtagc 79

<210> SEQ ID NO 37
<211> LENGTH: 79
<212> TYPE: DNA
<213> ORGANISM: Mycobacterium tuberculosis

<400> SEQUENCE: 37
accggatatc ttagctggtc aatagccatt tttcagcaat ttctcagtaa cgctacgggg 60
cgcgccgtgc cgtagtagc 79

<210> SEQ ID NO 38
<211> LENGTH: 79
<212> TYPE: DNA
<213> ORGANISM: Mycobacterium tuberculosis

<400> SEQUENCE: 38
accggatatc ttagctggtc aatagccatt tttcagcaat ttctcagtaa cgctacgggg 60
cgcgccgtgc cgtagtagc 79

-continued

```
<210> SEQ ID NO 39
<211> LENGTH: 79
<212> TYPE: DNA
<213> ORGANISM: Mycobacterium tuberculosis

<400> SEQUENCE: 39

accggatatc ttagctggtc aatagccatt tttcagcaat ttctcagtaa cgctacgggg     60

cgcgccgtgc cgtagtagc                                                  79
```